United States Patent
Johnson et al.

(10) Patent No.: US 12,359,166 B2
(45) Date of Patent: *Jul. 15, 2025

(54) TAURINE SUPPLEMENTED CELL CULTURE MEDIUM AND METHODS OF USE

(71) Applicant: Regeneron Pharmaceuticals, Inc., Tarrytown, NY (US)

(72) Inventors: Amy S. Johnson, Briarcliff Manor, NY (US); Meghan E. Casey, Ridgewood, NJ (US); Shadia Oshodi, Jersey City, NJ (US); Shawn Lawrence, Nyack, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/672,979

(22) Filed: May 23, 2024

(65) Prior Publication Data

US 2024/0309316 A1    Sep. 19, 2024

Related U.S. Application Data

(63) Continuation of application No. 18/371,959, filed on Sep. 22, 2023, which is a continuation of application No. 17/707,017, filed on Mar. 29, 2022, which is a continuation of application No. 15/749,037, filed as application No. PCT/US2016/045403 on Aug. 3, 2016, now Pat. No. 11,312,936.

(60) Provisional application No. 62/200,689, filed on Aug. 4, 2015.

(51) Int. Cl.
*C12N 5/00* (2006.01)
*C12N 15/79* (2006.01)

(52) U.S. Cl.
CPC ............ *C12N 5/0018* (2013.01); *C12N 15/79* (2013.01); *C12N 2500/33* (2013.01); *C12N 2500/74* (2013.01); *C12N 2500/80* (2013.01)

(58) Field of Classification Search
None
See application file for complete search history.

(56) References Cited

U.S. PATENT DOCUMENTS

| | | |
|---|---|---|
| 3,883,511 A | 5/1975 | Troonen et al. |
| 4,072,565 A | 2/1978 | Weiss et al. |
| RE30,985 E | 6/1982 | Cartaya et al. |
| 4,419,446 A | 12/1983 | Howley et al. |
| 4,560,655 A | 12/1985 | Baker et al. |
| 4,601,978 A | 7/1986 | Karin et al. |
| 4,615,977 A | 10/1986 | Hasegawa et al. |
| 4,657,866 A | 4/1987 | Kumar et al. |
| 4,676,980 A | 6/1987 | Segal et al. |
| 4,767,704 A | 8/1988 | Cleveland et al. |
| 4,786,599 A | 11/1988 | Chessebeuf et al. |
| 4,816,567 A | 3/1989 | Cabilly et al. |
| 4,927,762 A | 5/1990 | Darfler et al. |
| 4,965,199 A | 10/1990 | Capon et al. |
| 5,063,157 A | 11/1991 | Stockinger et al. |
| 5,122,469 A | 6/1992 | Mather et al. |
| 5,342,777 A | 8/1994 | Cole et al. |
| 5,426,699 A | 6/1995 | Wunderlich et al. |
| 5,529,920 A | 6/1996 | Cole et al. |
| 5,545,806 A | 8/1996 | Lonberg et al. |
| 5,545,807 A | 8/1996 | Surani et al. |
| 5,569,825 A | 10/1996 | Lonberg et al. |
| 5,571,894 A | 11/1996 | Wels et al. |
| 5,587,458 A | 12/1996 | King et al. |
| 5,610,279 A | 3/1997 | Brockhaus et al. |
| 5,625,126 A | 4/1997 | Lonberg et al. |
| 5,633,425 A | 5/1997 | Lonberg et al. |
| 5,641,870 A | 6/1997 | Rinderknecht et al. |
| 5,648,237 A | 7/1997 | Carter et al. |
| 5,661,016 A | 8/1997 | Lonberg et al. |
| 5,705,364 A | 1/1998 | Etcheverry et al. |
| 5,789,199 A | 8/1998 | Joly et al. |
| 5,811,299 A | 9/1998 | Renner et al. |
| 5,840,523 A | 11/1998 | Simmons et al. |
| 5,856,179 A | 1/1999 | Chen et al. |
| 5,869,046 A | 2/1999 | Presta et al. |
| 5,959,177 A | 9/1999 | Hein et al. |
| 5,976,833 A | 11/1999 | Furukawa et al. |
| 6,043,092 A | 3/2000 | Block et al. |

(Continued)

FOREIGN PATENT DOCUMENTS

| | | |
|---|---|---|
| CA | 2045208 C | 11/2003 |
| CA | 2091636 C | 2/2004 |

(Continued)

OTHER PUBLICATIONS

Kelley, B. (Sep./Oct. 2009). Industrialization of mAb Production Technology, mAbs, vol. 1, No. 5, pp. 443-452.

Kim et al., Development of serum-free medium supplemented with hydrolysates for the production of therapeutic antibodies in CHO cell cultures using design of experiments, Applied Microbiology and Biotechnology, 2009, vol. 83, pp. 639-648.

Kipriyanov et al., Recombinant single-chain Fv fragments carrying C-terminal cysteine residues: Production of bivalent and biotinylated miniantibodies, Mol. Immunol., 1994, 31(14):1047-1058.

Kipriyanov et al., Single-chain antibody streptavidin fusions: tetrameric bifunctional scFv-complexes with biotin binding activity and enhanced affinity to antigen, Human Antibodies and Hybridomas (1995) 6:93-101.

(Continued)

*Primary Examiner* — Christopher M Babic
*Assistant Examiner* — Kimberly A Aron
(74) *Attorney, Agent, or Firm* — Herbert Smith Freehills Kramer (US) LLP

(57) ABSTRACT

The specification describes a composition comprising an improved eukaryotic cell culture medium, which can be used for the production of a protein of interest. TaXULne can be added to the serum-free media or chemically-defined media to increase the production of a protein of interest. Methods for recombinantly expressing high levels of protein using the media compositions are included.

29 Claims, 1 Drawing Sheet

(56) References Cited

U.S. PATENT DOCUMENTS

| | | | |
|---|---|---|---|
| 6,048,728 A | 4/2000 | Inlow et al. |
| 6,087,123 A | 7/2000 | Wissler et al. |
| 6,146,847 A | 11/2000 | Goffe et al. |
| 6,171,586 B1 | 1/2001 | Lam et al. |
| 6,180,401 B1 | 1/2001 | Chen et al. |
| 6,248,516 B1 | 6/2001 | Winter et al. |
| 6,267,958 B1 | 7/2001 | Andya et al. |
| 6,417,429 B1 | 7/2002 | Hein et al. |
| 6,420,548 B1 | 7/2002 | Vezina et al. |
| 6,528,286 B1 | 3/2003 | Ryll et al. |
| 6,589,759 B1 | 7/2003 | Loscalzo et al. |
| 6,924,124 B1 | 8/2005 | Singh et al. |
| 6,927,004 B2 | 8/2005 | Eurlings et al. |
| 7,070,959 B1 | 7/2006 | Papadopoulos et al. |
| 7,078,492 B2 | 7/2006 | Pirofski et al. |
| 7,087,411 B2 | 8/2006 | Daly et al. |
| 7,105,348 B2 | 9/2006 | Murphy et al. |
| 7,125,978 B1 | 10/2006 | Vezina et al. |
| 7,153,507 B2 | 12/2006 | van de Winkel et al. |
| 7,189,826 B2 | 3/2007 | Rodman et al. |
| 7,279,159 B2 | 10/2007 | Daly et al. |
| 7,294,484 B2 | 11/2007 | Drapeau et al. |
| 7,303,694 B2 | 12/2007 | Murphy et al. |
| 7,371,922 B2 | 5/2008 | Wheeler et al. |
| 7,429,491 B2 | 9/2008 | Luan et al. |
| 7,435,553 B2 | 10/2008 | Fandl et al. |
| 7,455,988 B2 | 11/2008 | Fandl et al. |
| 7,582,298 B2 | 9/2009 | Stevens et al. |
| 7,666,416 B2 | 2/2010 | Etcheverry et al. |
| 7,750,138 B2 | 7/2010 | Fang et al. |
| 7,771,997 B2 | 8/2010 | Chen et al. |
| 7,879,984 B2 | 2/2011 | Martin et al. |
| 7,951,577 B2 | 5/2011 | Murphy et al. |
| 8,021,881 B2 | 9/2011 | Reiter et al. |
| 8,043,617 B2 | 10/2011 | Stevens et al. |
| 8,062,640 B2 | 11/2011 | Sleeman et al. |
| 8,216,575 B2 | 7/2012 | Yu et al. |
| 8,309,088 B2 | 11/2012 | MacDonald et al. |
| 8,313,926 B2 | 11/2012 | Grillberger et al. |
| 8,637,312 B2 | 1/2014 | Krueger et al. |
| 8,735,095 B2 | 5/2014 | Martin et al. |
| 8,871,209 B2 | 10/2014 | Stitt et al. |
| 8,945,559 B2 | 2/2015 | Dix et al. |
| 9,018,356 B2 | 4/2015 | Sleeman et al. |
| 9,045,536 B2 | 6/2015 | Merchant et al. |
| 9,079,948 B2 | 7/2015 | Orengo et al. |
| 9,127,265 B2 | 9/2015 | Grillberger et al. |
| 9,132,192 B2 | 9/2015 | Daly et al. |
| 9,150,645 B2 | 10/2015 | Subramanian et al. |
| 9,173,380 B2 | 11/2015 | Trenkle et al. |
| 9,173,880 B2 | 11/2015 | Dix et al. |
| 9,181,572 B2 | 11/2015 | Subramanian et al. |
| 9,217,168 B2 | 12/2015 | Prentice et al. |
| 9,228,014 B2 | 1/2016 | Classon et al. |
| 9,260,515 B2 | 2/2016 | Stitt et al. |
| 9,265,827 B2 | 2/2016 | Wiegand et al. |
| 9,266,949 B2 | 2/2016 | Ramasubramanyan et al. |
| 9,302,015 B2 | 4/2016 | Papadopoulos et al. |
| 9,353,176 B2 | 5/2016 | MacDonald et al. |
| 9,359,434 B2 | 6/2016 | Subramanian et al. |
| 9,402,898 B2 | 8/2016 | Walsh et al. |
| 9,447,431 B2 | 9/2016 | Thess et al. |
| 9,499,616 B2 | 11/2016 | Subramanian et al. |
| 9,644,181 B2 | 5/2017 | Matsuyama et al. |
| 9,663,810 B2 | 5/2017 | Prentice et al. |
| 9,714,411 B2 | 7/2017 | Grillberger et al. |
| 9,758,568 B2 | 9/2017 | Grillberger et al. |
| 9,809,796 B2 | 11/2017 | Gillberger et al. |
| 10,927,342 B2 | 2/2021 | Johnson et al. |
| 2004/0107454 A1 | 6/2004 | Wheeler et al. |
| 2005/0026229 A1 | 2/2005 | Reiter et al. |
| 2005/0100546 A1 | 5/2005 | Jakobovits et al. |
| 2005/0272124 A1 | 12/2005 | Chen et al. |
| 2005/0287149 A1 | 12/2005 | Keler et al. |
| 2006/0059575 A1 | 3/2006 | Kusunoki et al. |
| 2006/0094104 A1 | 5/2006 | Grillberger et al. |
| 2006/0094113 A1 | 5/2006 | Epstein et al. |
| 2006/0147426 A1 | 7/2006 | Schiller et al. |
| 2006/0183887 A1 | 8/2006 | Jakobovits et al. |
| 2006/0258841 A1 | 11/2006 | Michl et al. |
| 2007/0212770 A1 | 9/2007 | Grillberger et al. |
| 2007/0212778 A1 | 9/2007 | Bramke et al. |
| 2008/0008695 A1 | 1/2008 | Vellard et al. |
| 2008/0131410 A1 | 6/2008 | Hariri et al. |
| 2008/0254513 A1* | 10/2008 | Cayli ............... C12N 5/0018 435/70.1 |
| 2008/0274507 A1 | 11/2008 | Gomes et al. |
| 2009/0137416 A1 | 5/2009 | Fandl et al. |
| 2009/0162901 A1 | 6/2009 | Chen et al. |
| 2009/0191591 A1 | 7/2009 | Tabuchi et al. |
| 2010/0167346 A1 | 7/2010 | Tabuchi et al. |
| 2010/0227819 A1 | 9/2010 | Hernandez et al. |
| 2010/0285533 A1 | 11/2010 | Krueger et al. |
| 2010/0304436 A1 | 12/2010 | Chen et al. |
| 2010/0331527 A1 | 12/2010 | Davis et al. |
| 2011/0229933 A1 | 9/2011 | Krishnan et al. |
| 2012/0034674 A1 | 2/2012 | Grillberger et al. |
| 2012/0129727 A1 | 5/2012 | Hossler et al. |
| 2012/0171161 A1 | 7/2012 | Abramson et al. |
| 2012/0258533 A1 | 10/2012 | Bredahl et al. |
| 2012/0264170 A1 | 10/2012 | Merchant et al. |
| 2013/0224855 A1 | 8/2013 | Gupta et al. |
| 2013/0344535 A1 | 12/2013 | Mundt et al. |
| 2014/0044730 A1 | 2/2014 | Yancopoulos et al. |
| 2014/0088295 A1 | 3/2014 | Smith et al. |
| 2014/0127227 A1 | 5/2014 | Chang et al. |
| 2014/0271642 A1 | 9/2014 | Murphy et al. |
| 2014/0271653 A1 | 9/2014 | Gurnett-Bander et al. |
| 2014/0271658 A1 | 9/2014 | Murphy et al. |
| 2014/0271681 A1 | 9/2014 | Martin et al. |
| 2014/0273095 A1 | 9/2014 | Oshodi et al. |
| 2014/0314779 A1 | 10/2014 | Vijayasankaran et al. |
| 2015/0203579 A1 | 7/2015 | Papadopoulos et al. |
| 2015/0203580 A1 | 7/2015 | Papadopoulos et al. |
| 2015/0216795 A1 | 8/2015 | Assadourian et al. |
| 2015/0259423 A1 | 9/2015 | Kirshner et al. |
| 2015/0266966 A1 | 9/2015 | Smith et al. |
| 2015/0275230 A1 | 10/2015 | Tabuchi et al. |
| 2015/0313194 A1 | 11/2015 | Hu et al. |
| 2015/0337029 A1 | 11/2015 | Kyratsous et al. |
| 2015/0337045 A1 | 11/2015 | Okamoto et al. |
| 2016/0017029 A1 | 1/2016 | Walsh et al. |
| 2016/0075778 A1 | 3/2016 | Okamoto et al. |
| 2016/0076068 A1 | 3/2016 | Engel et al. |
| 2016/0083689 A1 | 3/2016 | Grillberger et al. |
| 2016/0215040 A1 | 7/2016 | Kyratsous et al. |
| 2016/0237400 A1 | 8/2016 | Xian et al. |
| 2016/0333385 A1 | 11/2016 | Kang et al. |
| 2017/0107553 A1 | 4/2017 | Kottakota et al. |
| 2017/0305999 A1 | 10/2017 | Leber et al. |
| 2018/0298078 A1 | 10/2018 | Park et al. |
| 2018/0346881 A1 | 12/2018 | Clemens et al. |
| 2018/0355038 A1 | 12/2018 | Smith et al. |
| 2019/0010531 A1 | 1/2019 | Chen et al. |
| 2020/0131554 A1 | 4/2020 | Chen et al. |
| 2020/0149081 A1 | 5/2020 | Oshodi et al. |
| 2020/0157492 A1 | 5/2020 | Johnson et al. |
| 2020/0255880 A1 | 8/2020 | Chen et al. |
| 2021/0332402 A1 | 10/2021 | Oshodi et al. |
| 2021/0388407 A1 | 12/2021 | Chen et al. |
| 2021/0388408 A1 | 12/2021 | Chen et al. |

FOREIGN PATENT DOCUMENTS

| | | |
|---|---|---|
| CN | 1241573 A | 1/2000 |
| CN | 1367258 A | 9/2002 |
| CN | 101065480 A | 10/2007 |
| CN | 101220347 A | 7/2008 |
| CN | 101360820 A | 2/2009 |
| CN | 101603026 A | 12/2009 |
| CN | 102093978 A | 6/2011 |
| CN | 102224239 A | 10/2011 |
| CN | 102317440 A | 1/2012 |
| DE | 266710 A3 | 12/1989 |

(56) References Cited

FOREIGN PATENT DOCUMENTS

| | | |
|---|---|---|
| EP | 0183070 A2 | 6/1986 |
| EP | 0244234 A2 | 11/1987 |
| EP | 0307247 A2 | 3/1989 |
| EP | 0308936 A2 | 3/1989 |
| EP | 0073657 B1 | 12/1990 |
| EP | 0402226 A1 | 12/1990 |
| EP | 0591605 A2 | 4/1994 |
| EP | 1321515 A1 | 6/2003 |
| EP | 2921554 A1 | 9/2015 |
| EP | 2971040 B1 | 9/2018 |
| JP | H07507446 A | 8/1995 |
| JP | 2013208104 A | 10/2013 |
| RU | 2192884 C2 | 11/2002 |
| WO | 8700195 A1 | 1/1987 |
| WO | 9003430 A1 | 4/1990 |
| WO | 9013646 A1 | 11/1990 |
| WO | 9100360 A1 | 1/1991 |
| WO | 9110741 A1 | 7/1991 |
| WO | 9209298 A1 | 6/1992 |
| WO | 9209690 A2 | 6/1992 |
| WO | 9220373 A1 | 11/1992 |
| WO | 9306213 A1 | 4/1993 |
| WO | 9308829 A1 | 5/1993 |
| WO | 9316185 A2 | 8/1993 |
| WO | 9318143 A1 | 9/1993 |
| WO | 9404690 A1 | 3/1994 |
| WO | 9411026 A2 | 5/1994 |
| WO | 9607754 A1 | 3/1996 |
| WO | 9627011 A1 | 9/1996 |
| WO | 9633735 A1 | 10/1996 |
| WO | 9634096 A1 | 10/1996 |
| WO | 9824893 A2 | 6/1998 |
| WO | 9845411 A1 | 10/1998 |
| WO | 9859035 A2 | 12/1998 |
| WO | 9935255 A2 | 7/1999 |
| WO | 9964578 A1 | 12/1999 |
| WO | 0075319 A1 | 12/2000 |
| WO | 02101019 A2 | 12/2002 |
| WO | 2005028626 A2 | 3/2005 |
| WO | 2006044908 A2 | 4/2006 |
| WO | 2006089232 A2 | 8/2006 |
| WO | 2006116034 A1 | 11/2006 |
| WO | 2006116369 A2 | 11/2006 |
| WO | 2007050498 A2 | 5/2007 |
| WO | 2007077217 A1 | 7/2007 |
| WO | 2007146123 A2 | 12/2007 |
| WO | 2008063892 A2 | 5/2008 |
| WO | 2008154014 A2 | 12/2008 |
| WO | 2009020144 A1 | 2/2009 |
| WO | 2011008770 A2 | 1/2011 |
| WO | 2011019619 A1 | 2/2011 |
| WO | 2011079004 A1 | 6/2011 |
| WO | 2012091124 A1 | 7/2012 |
| WO | 2013184809 A1 | 12/2013 |
| WO | 2014020160 A1 | 2/2014 |
| WO | 2014029772 A1 | 2/2014 |
| WO | 2014058025 A1 | 4/2014 |
| WO | 2014144198 A1 | 9/2014 |
| WO | 2014154098 A1 | 9/2014 |
| WO | 2015105609 A1 | 7/2015 |
| WO | 2015105926 A1 | 7/2015 |
| WO | 2019010191 A1 | 1/2019 |

OTHER PUBLICATIONS

Kohler, G. et al. (Aug. 7, 1975). Continuous Cultures of Fused Cells Secreting Antibody of Predefined Specificity, Nature, vol. 256, pp. 495-497.
Korang et al., Levels of taurine, amino acids and related compounds in plasma, vena cava, aorta and heart of rats after taurine administration, Pharmacology, 1996, 52(4):263-270 (Abstract only).
Kostelny, S.A. et al. (Mar. 1, 1992). Formation of a Bispecific Antibody by the Use of Leucine Zippers, J. Immunol., vol. 148, No. 5, pp. 1547-1553.
Kou et al., Increasing the productivity of TNFR-Fc in GS-CHO cells at reduced culture temperatures, Biotechnology and Bioprocess Engineering, 2011, vol. 16, pp. 136-143.
Kozbor, D. (Dec. 1984). A Human Hybrid Myeloma For Production of Human Monoclonal Antibodies, J. Immunol., vol. 133, No. 6, pp. 3001-3005.
Kucharzewska et al., Ornithine decarboxylase and extracellular polyamines regulate microvascular sprouting and actin cytoskeleton dynamics in endothelial cells, Experimental Cell Research (2010) 316: 26-83-2691.
Kumar et al., Differential protein expression following low temperature culture of suspension CHO-K1 cells, BMC Biotechnology, 2008, 8:42, 13 pages.
Kyriakopoulous, S. et al., Comparative Analysis of Amino Acid Metabolism and Transport in CHO Variants with Different Levels of Productivity Journal of Biotechnology (2013) vol. 168, pp. 543-551.
Lee, C.V. et al. (2004). Bivalent Antibody Phage Display Mimics Natural Immunoglobulin, J. Immunol. Methods, vol. 284, Nos. 1-2, pp. 119-132.
Lee, C.V. et al. (2004). High-Affinity Human Antibodies From Phage-displayed Synthetic Fab Libraries with a Single Framework Scaffold, J. Mol. Biol., vol. 340, No. 5, pp. 1073-1093.
Leon, R. et al., Protective Function of Taurine in Glutamate-Induced Apoptosis in Cultured Neurons Journal of Neuroscience Research (2009) vol. 87, pp. 1185-1194.
Matsuoka et al., Improvement of production rate on recombinant CHO cells in two-stage culture, BMC Proceedings, 2013, 7(Suppl 6):P50, 2 pages.
Nagae et al., Function and 3D Structure of the N-Glycans on Glycoproteins, Int. J Mol. Sci. 2012, 13, 8398-8429.
Oguchi et al., pH Condition in temperature shift cultivation enhances cell longevity and specific hMab productivity in CHO culture, Cytotechnology, 2006, 52: 199-207.
Ornithine, Wikipedia, 3 pages, retrieved from https://en.wikipedia.org/wiki/Ornithine on May 11, 2020.
Gao et al., The role of mitochondrial permeability transition in apoptosis induced by taurine deficiency, Feed Industry, 2013, 34(9), 18-21 (with English abstract).
Hoogenboom et al. (2001). Methods in Molecular Biology O'Brien et al., Eds., Humana Press: Totowa, N.J. vol. 178, pp. 1-37.
International Preliminary Report on Patentability Issued in PCT/US2016/045403 dated Feb. 6, 2018, 7 pages.
International Search Report and Written Opinion Issued in PCT/US2016/045403 dated Oct. 4, 2016, 10 pages.
International Search Report dated Jul. 24, 2014, for PCT Application No. PCT/US2014/029772, filed on Mar. 14, 2014, 3 pages.
Written Opinion dated Jul. 24, 2014, for PCT Application No. PCT/US2014/029772, filed on Mar. 14, 2014, 11 pages.
Bass, S. S et al. (1990). "Hormone Phage: An Enrichment Method for Variant Proteins with Altered Binding Properties," Proteins, vol. 8, No. 4, pp. 309-314.
Bettger et al., "Rapid clonal growth and serial passage of human diploid fibroblasts in a lipid-enriched synthetic medium supplemented with epidermal growth factor, insulin, and dexamethasone," Proc. Natl. Acad. Sci. USA, 1981, 78(9), pp. 5588-5592.
Boerner, P. et al. (1991). "Production of Antigen-Specific Human Monoclonal Antibodies From in Vitro-primed Human Splenocytes," J. Immunol., vol. 147, No. 1, pp. 86-95.
Bokati et al., "Corrosion inhibition of copper, mild steel and galvanically coupled coppermild steel in artificial sea water in presence of 1H-benzotriazole, sodium molybdate and sodium phosphate," Corrosion Science (2017) 126:272-285.
Branca et al., "Inhibition of Ornithine Decarboxylase of HeLa Cells by Diamines and Polyamines," Biochem. J. (1980) 186, 925-931.
Brasel et al., "Hematologic Effects of flt3 Ligand In Vivo in Mice," Blood, 1996, 88(6), pp. 2004-2012.
Brennan, M. et al. (Jul. 5, 1985). "Preparation of Bispecific Antibodies by Chemical Recombination of Monoclonal Immunoglobulin G1 Fragments," Science, vol. 229, pp. 81-83.
Brodeur, B.R. et al. (1987). "Mouse-Human Myeloma Partners for the Production of Heterohybridomas," Chapter 4 in Monoclonal Antibody Production Techniques and Applications, Marcel Dekker, Inc.: New York, New York, pp. 51-63.

(56) References Cited

OTHER PUBLICATIONS

Bruggemann, M. et al. (1993). "Designer Mice: The Production of Human Antibody Repertoires in Transgenic Animals," Year in Immuno., vol. 7, pp. 33-40.
Byrn et al., "Biological properties of a CD4 immunoadhesin," Nature (1990) 344:667-670.
Carter, P. et al. (Feb. 1992). "High Level *Escherichia coli* Expression and Production of a Bivalent Humanized Antibody Fragment," Bio/Technology, vol. 10, pp. 163-167.
Carter, P. et al. (May 1992). "Humanization of an Anti-p185HEH2 Antibody for Human Cancer Therapy," Proc. Natl. Acad. Sci. USA, vol. 89, p. 4285.
Charlton, K.A. (2003). "Methods in Molecular Biology," Lo, B.K. C. ed., Humana Press: Totowa, NJ, pp. 245-254.
Chothia, C. et al. (1987). "Canonical Structures for the Hypervariable Regions of Immunoglobulins," J. Mol. Biol., vol. 196, pp. 901-917.
Clackson, T. et al. (Aug. 15, 1991). "Making Antibody Fragments Using Phage Display Libraries," Nature, vol. 352, pp. 624-628.
Cozzi, R. et al., "Taurine and Ellagic Acid: Two Differently-Acting Natural Antioxidants" Environmental and Molecular Mutagenesis (1995) vol. 26, pp. 248-254.
Daugherty, A.L. et al. (2006). "Formulation and Delivery Issues for Monoclonal Antibody Therapeutics," Adv. Drug Deliver. Rev., vol. 58, Nos. 5-6, pp. 686-706.
Davidson et al., "The Nucleoprotein Content of Fibroblasts Growing in vitro," Biochem. J., 1945, 39(2), pp. 188-199.
Declerck and Tebbey, "Importance of manufacturing consistency of the glycosylated monoclonal antibody adalimumab (Humira®) and potential impact on the clinical use of biosimilars," Generics and Biosimilars Initiative Journal (2016) 5:2, pp. 70-73.
Duchosal, M.A. et al. (Jan. 16, 1992). "Immunization of hu-PBL-SCID Mice and the Rescue of Human Monoclonal Fab Fragments Through Combinatorial Libraries," Nature, vol. 355, No. 6357, pp. 258-262.
Dulbecco et al., "Production of Plaques in Monolayer Tissue Cultures by Single Particulars of an Animal Virus," Proc. Natl. Acad. Sci. USA, 1952, 38(8), pp. 747-752.
Eagle et al., "Nutrition Needs of Mammalian Cells in Tissue Culture," Science, 1955, 122(3168), pp. 501-504.
Embleton, M.J. et al. (Aug. 11, 1992). "In-Cell PCR From mRNA: Amplifying and Linking The Rearranged Immunoglobulin Heavy and Light Chain V-Genes Within Single Cells," Nucl. Acids Res., vol. 20, No. 15, pp. 3831-3837.
Eremeeva, M.E. et al. (May 1, 1998). "Effects of the Antioxidant alpha-lipoic Acid on Human Umbilical Vein Endothelial Cells Infected with Rickettsia rickettsii," Infection and Immunity, vol. 66, No. 5, pp. 2290-2299.
Even, M.S. et al. (Mar. 2006). "Serum-Free Hybridoma Culture: Ethical Scientific and Safety Considerations," Trends in Biotechnology, vol. 24, No. 3, pp. 105-108.
Fan, Y. et al., "Amino acid and glucose metabolism in fed-batch CHO cell culture affects antibody production and glycosylation," Biotechnol Bioeng. Mar. 2015; 112(3):521-35, 50 pages provided.
Fellouse, F.A. et al. (Aug. 24, 2004). "Synthetic Antibodies From a Four-Amino-Acid Code: A Dominant Role for Tyrosine in Antigen Recognition," Proc. Natl. Acad. Sci. USA, vol. 101, No. 34, pp. 12467-12472.
Fishwild, D.M. et al. (Jul. 1996). "High-avidity Human IgGK Monoclonal Antibodies From a Novel Strain of Minilocus Transgenic Mice," Nature Biotechnol., vol. 14, pp. 845-851.
Fleer, R. et al. (Oct. 1991). "Stable Multicopy Vectors for High-Level Secretion of Recombinant Human Serum Albumin by Kluyveromyces Yeasts," Bio/Technology, vol. 9, pp. 968-975.
Franek et al., "Plant Protein Hydrolysates: Preparation of Defined Peptide Fractions Promoting Growth and Production in Animal Cells Cultures," Biotechnol. Prog. 16 (5):688-92 (2000).
Franek, F., "Oligopeptides as Tools for Improving Productivity of Hybridoma Cells Cultures" (2005). Trends in Monoclonal Antibody Research (2005) pp. 111-121.

Froud et al., "Polyamine enhanced product expression from transformed and recombinant cell lines," Production of Biologicals from Animal Cells in Culture (Editors: Spier et al.), Butterworth-Heinemann Ltd, Oxford, 1991, pp. 107-109.
Fusi et al., "Effects of putrescine, cadaverine, spermine, spermidine, and ß-phenylethylamine on cultured bovine mammary epithelial cells," Ital. J. Anim. Sci., vol. 7, 131-140, 2008.
Gahl et al., "Reversal by aminoguanidine of the inhibition of proliferation of human fibroblasts by spermidine and spermine," Chem.-Biol Interactions, 22 (1978) 91-98.
Gerngross, T.U. (Nov. 2004). "Advances in the Production of Human Therapeutic Proteins in Yeasts and Filamentous Fungi," Nat. Biotech., vol. 22, No. 11, pp. 1409-1414.
Goding, J.W. (1983). "Production of Monoclonal Antibodies," Chapter 3 in Monoclonal Antibodies: Principles and Practice Academic Press., pp. 56-103, Table of Contents p. vii-ix.
Google® Scholar search, "a trap molecule" pp. 1-2; Jul. 23, 2020.
Leung, D.W. et al. (1989). "A Method for Random Mutagenesis of a Defined DNA Segment Using a Modified Polymerase Chain Reaction", Technique, vol. 1, pp. 11-15.
Li and Wen, "Screening soy hydrolysates for the production of a recombinant therapeutic protein in commercial cell line by combined approach of near-infrared spectroscopy and chemometrics," Appl Microbiol Biotechnol (2013) 97:2653-2660.
Li F. et al. (Sep./Oct. 2010). "Cell Culture Processes for Monoclonal Antibody Production," mAbs, vol. 2, No. 5, pp. 466-477.
Li, H. et al. (Feb. 2006, e-pub. Jan. 22, 2006). "Optimization of Humanized IgGs in Glycoengineered Pichia Pastoris," Nat. Biotech., vol. 24, No. 2, pp. 210-215.
Lindmark, R. et al. (1983). "Binding of Immunoglobulins to Protein A and Immunoglobulin Levels in Mammalian Sera," J. Immunol. Methods., vol. 62, pp. 1-13.
Lonberg, N. et al. (1995). "Human Antibodies From Transgenic Mice," Intern. Rev. Immunol., vol. 13, pp. 65-93.
Lonberg, N. et al. (Apr. 28, 1994). "Antigen-Specific Human Antibodies from Mice Comprising Four Distinct Genetic Modifications," Nature, vol. 368, pp. 856-859.
Marks, J.D. et al. (1991). "By-Passing Immunization: Human Antibodies from V-gene Libraries Displayed on Phage," J. Mol. Biol., vol. 222, pp. 581-597.
Marks, J.D. et al. (Jul. 1992). "By-Passing Immunization: Building Affinity Human Antibodies by Chain Shuffling," Bio/Technology, vol. 10, pp. 779-783.
Mather, J.P. (1980). "Establishment and Characterization of Two Distinct Mouse Testicular Epithelial Cell Lines," Biol. Reprod., vol. 23, pp. 243-251.
Mather, J.P. et al. (1982). "Culture of Testicular Cells in Hormone-Supplemented Serum-Free Medium," Annals NY Acad. Sci., vol. 383, pp. 44-68.
Matsuda, F. et al. (Jan. 1993). "Structure and Physical Map of 64 Variable Segments in the 3' 0.8-Megabase Region of the Human Immunoglobulin Heavy-Chain Locus," Nature Genet., vol. 3, No. 1, pp. 88-94.
McKinnon et al., "Expression, purification and characterization of secreted recombinant human insulin-like growth factor I (IGF-1) and the potent variant des(1-3)IGF-1 in Chinese hamster ovary cells," J. Mol. Endocrinol., 1991, 6, pp. 231-239.
Mehta, T.R. et al., "Taurine is a Weak Scavenger of Peroxynitrite and Does Not Attenuate Sodium Nitroprusside Toxicity to Cells in Culture," Amino Acids (2001), vol. 20, No. 4, pp. 419-433.
Miao, J. et al., "Taurine attenuates lipopolysaccharide-induced disfunction in mouse mammary epithelial cells", Cytokine, Academic Press Ltd. (2012), vol. 59, No. 1, pp. 35-40.
Michael, A.J., "Biosynthesis of polyamines and polyamine containing molecules," Biochem. J. (2016) 473, 2315-2329.
Milstein, C. et al. (Oct. 6, 1983). "Hybrid Hybridomas and Their Use in Immunohistochemistry," Nature, vol. 305, pp. 537-539.
Moore and Stein, "A Modified Ninhydrin Reagent for the Photometric Determination of Amino Acids and Related Compounds," J. Biol. Chem. 1954, vol. 211, pp. 907-913.
Moore et al., "Culture of Normal Human Leukocytes," J. Amer. Med. Assoc., 1967, 199(8), pp. 519-524.

(56) References Cited

OTHER PUBLICATIONS

Morimoto, K. et al. (1992). "Single-Step Purification of F(ab')2 Fragments of Mouse Monoclonal Antibodies (Immunoglobulins G1) by Hydrophobic Interaction Higtl Performance Liquid Chromatography Using TSKgel Phenyl-5PW," Journal of Biochemical and Biophysical Methods, vol. 24, pp. 107-117.
Morrison and Seidel, "Cell spreading and the regulation of ornithine decarboxylase," Journal of Cell Science (1995) 108: 3787-3794.
Morrison, S.L. (Apr. 28, 1994). "Success in Specification," Nature, vol. 368, pp. 812-813.
Morrison, S.L. et al. (Nov. 1984). "Chimeric Human Antibody Molecules: Mouse Antigen-Binding Domains with Human Constant Region Domains," Proc. Natl. Acad. Sci, vol. 81, pp. 6841-6855.
Mrsny, R.J. et al., "Inhibition of Hamster Sperm Na+, K+-ATPase Activity by Taurine and Hypotaurine", Life Sciences (1985), vol. 36, No. 3, pp. 271-275.
Munson, P.J. et al. (1980). "Ligand: A Versatile Computerized Approach for Characterization of Ligand-Binding Systems," Analy. Biochem., vol. 107, pp. 220-239.
Nemkov et al., "Three-minute method for amino acid analysis by UHPLC and high-resolution quadrupole orbitrap mass spectrometry," Amino Acids, 2015, 47(11):2345-2357, 23 pages provided.
Neuberger, M. (Jul. 1996). "Generating High-Avidity Human Mabs in Mice," Nature Biotechnol., vol. 14, p. 826.
Ni, J. (2006). "Research progress and future perspectives in antibodomics and antibodomic Drugs", Xiandai Mian Yixue, vol. 26, No. 4, pp. 265-268. (with English machine translation Abstract).
Orlandi, R. et al. (May 1989). "Cloning Immunoglobulin Variable Domains for Expression by the Polymerase Chain Reaction," Proc. Natl. Acad. Sci. USA, vol. 86, pp. 3833-3837.
Orr et al., "Survival of Animal Tissue Cells in Primary Culture in the Absence of Serum," Appl. Microbiol., 1973, 25(1), pp. 49-54.
Orum H. et al. (Sep. 24, 1993). "Efficient Method for Constructing Comprehensive Murine Fab Antibody Libraries Displayed on Phage," Nucleic Acids Res., vol. 21, No. 19, pp. 4491-4498.
Pubchem, "Taurine Computed Properties," retrieved from https://pubchem.ncbi.nlm.nih.gov/compound/Taurine on Jul. 30, 2020, 1 page.
Pastorian et al., Tolerance to Putrescine Toxicity in Chinese Hamster Ovary Cells Is Associated with Altered Uptake and Export, Experimental Cell Research, 231, 284-295 (1997).
Patkar, A. et al. (Feb. 28, 2002). Flow Cytometry as a Useful Tool for Process Development: Rapid Evaluation of Expression Systems, J. Biotechnology, vol. 93, No. 3, pp. 217-229.
Pegg, Regulation of Ornithine Decarboxylase, J. of Biol. Chem., May 2006, 281:21, pp. 14529-14532.
Pegg, Toxicity of Polyamines and Their Metabolic Products, Chemical Research in Toxicology, 2013, 26, 1782-1800.
Petters et al., Addition of Taurine of Hypotaurine to Culture medium Improves Development of One-and Two-Cell Pig Embryos in Vitro, Theriogenology (1991), vol. 35, No. 1, p. 253.
Pluckthun, A. (1992). Mono-and Bivalent Antibody Fragments Produced in *Escherichia coli*: Engineering, Folding and Antigen Binding, Immunol Revs., vol. 130, pp. 151-188.
Poljak, RJ, Production and structure of diabodies, Structure, Dec. 1994, 2:1121-1123.
Presta, L.G. et al. (Sep. 1, 1993). Humanization of an Antibody Directed Against IgE, J. Immunol., vol. 151, No. 5, pp. 2623-2632.
Purwaha et al., Targeted metabolomic analysis of amino acid response to L-*asparaginase* in adherent cells, Metabolomics (2014) 10:909919.
Putrescine, Wikipedia, 5 pages, retrieved from https://en.wikipedia.org/wiki/Putrescine on May 11, 2020.
Raafay et al., Aflibercept: a Potent Vascular Endothelial Growth Factor Antagonist for Neovascular Age-Related Macular Degeneration and Other Retinal Vascular Diseases, Biol Ther, 2012, 2:3, 22 pages.
Rasmussen et al., Isolation, characterization and recombinant protein expression in Veggie-CHO: a serum-free CHO host cell line, Cytotechnology, 1998, 28: 31-42.
Reyes, G.R. et al. (Jun. 17, 1982). Expression of Human -interferon cDNA Under the Control of a Thymidine Kinase Promoter from Herpes Simplex Virus, Nature, vol. 297, pp. 598-601.
Richardson et al., Metabolomics Analysis of Soy Hydrolysates for the Identification of Productivity Markers of Mammalia Cells for Manufacturing Therapeutic Proteins, Biotechnol. Prog., 2015, 31:522-531.
Riechmann, L. et al. (Mar. 24, 1988). Reshaping Human Antibodies for Therapy, Nature, vol. 332, pp. 323-329.
Ripps, H. et al., Review: Taurine: A very essential Amino Acid Molecular Vision (2012) vol. 18, pp. 2673-2686.
Ritacco et al., Cell Culture Media for Recombinant Protein Expression in Chinese Hamster Ovary (CHO) Cells: History, Key Components, and Optimization Strategies, Biotechnol Prog., 2018, vol. 34, No. 6, pp. 1407-1426.
Rodrigues et al., Comparison of commercial serum-free media for CHO-K1 cell growth and monoclonal antibody production, International Journal of Pharmaceutics (2012) 437: 303-305.
Rohrer et al., Profiling N-linked oligosaccharides from IgG by high-performance anion-exchange chromatography with pulsed amperometric detection, Glycobiology, 2016, vol. 26, No. 6, 582-591.
Sarilumab, Wikipedia, 3 pages, downloaded May 25, 2020, retrieved from https://en.wikipedia.org/wiki/Sarilumab.
Sastry, L. et al. (Aug. 1989). Cloning of the Immunological Repertoire in *Escherichia coli* for Generation of Monoclonal Catalytic Antibodies: Construction of a Heavy Chain Variable Region-Specific cDNA Library, Proc. Natl. Acad. Sci. USA, vol. 86, No. 15, pp. 5728-5732.
Schaffer, S.W. et al., Clinical Significance of Taurine Amino Acids (2014) vol. 46, pp. 1-5.
Shalaby, M.R. et al. (Jan. 1, 1992). Development of Humanized Bispecific Antibodies Reactive with Cytotoxic Lymphocytes and Tumor Cells Overexpressing the HER2 Protoonogene, J. Exp. Med., vol. 175, pp. 217-225.
Shantz and Levin, Regulation of ornithine decarboxylase during oncogenic transformation: mechanisms and therapeutic potential, Amino Acids (2007) 33: 213-223.
Shi et al., A High-throughput Automated Platform for the Development of Manufacturing Cell Lines for Protein Therapeutics, Journal of Visualized Experiments, Sep. 2011, 55, e3010, 5 pages.
Sidhu, S.S. et al. (2004). Phage-Displayed Antibody Libraries of Synthetic Heavy Chain Complementarity Determining Regions, J. Mol. Biol., 338, No. 2, pp. 299-310.
Sigma-Aldrich, Ethylenediaminetetraacetic acid tetrasodium salt dihydrate, downloaded May 26, 2020, 3 pages, retrieved from https://www.sigmaaldrich.com/catalog/product/sigma/e6511?lang=en&region=US.
Sigma-Aldrich, Nutrient Mixture F-12 Ham Formulation, Jan. 18, 2009, 7 pages, retrieved from https://www.sigmaaldrich.com/life-science/cell-culture/learning-center/media-formulations/f-12-ham.html on Apr. 12, 2019.
Sims, M.J. et al. (Aug. 15, 1993). A Humanized CD18 Antibody Can Block Function Without Cell Destruction, J. Immunol., vol. 151, No. 4, pp. 2296-2308.
Singer, M. et al. (1998). Genes and Genomes, Moscow, MIR, vol. 1, pp. 63-64 (with English machine translation).
Skerra, A. et al. (1993). Bacterial Expression of Immunoglobulin in Fragments, Curr. Opinion in Immunol., vol. 5, pp. 256-262.
Stinchcomb, D.T. et al. (Nov. 1, 1979). Isolation and Characterisation of a Yeast Chromosomal Replicator, Nature, vol. 282, pp. 39-43.
Stoner et al., Putrescine stimulates growth of human bronchial epithelial cells in primary culture, In Vitro, 1980, 16(5):399-406.
Suresh, M.R. et al. (1986). Bispecific Monoclonal Antibodies from Hybrid Hybridomas, Methods in Enzymology, vol. 121, pp. 210-228.
Tabuchi, H. et al., Cooeverexpression of Alanine Aminotransferase 1 in Chinese Hamster Ovary Cells Overexpressing Taurine Transporter Further Stimulates Metabolism and Enhances Product Yield Biotechnology and Bioengineering (2013) vol. 110, No. 8, pp. 2208-2215.

(56) References Cited

OTHER PUBLICATIONS

Tabuchi, H. et al., Overexpression of Taurine Transporter in Chinese Hamster Ovary Cells can Enhance Cell Biability and Product Yield, While Promoting Glutamine Consumption Biotechnology and Bioengineering (2010) vol. 107, No. 6, pp. 998-1003.
Takeuchi, K. et al.(Apr. 5, 200). A Hyperosmotic Stress-Induced mRNA of Carp Cell Encodes Dependent High Affinity Taurine Transporter, Biochim. Biophys. Acta, vol. 1464, No. 2, pp. 219-230.
Taurine Computed Properties. Downloaded from https://pubchem.ncbi.nlm.nih.gov/compound. Taurine on Jul. 30, 2020. 1 page.
Taylor et al., A transgenic mouse that expresses a diversity of human sequence heavy and light chain immunoglobulins, Nucl. Acids Res., (1992) 20(23):6287-6295.
ThermoFisher Scientific, Technical Resources, 11320, DMEM/F-12, [online], Retrieved from the Internet: <URL: http://www.thermofisher.com/us/en/home/technical-resources/media-formulation.55.html>, Retrieved from the Internet on Jan. 29, 2018, 3 pages.
Tobias et al., Exposure to Ornithine Results in Excessive Accumulation of Putrescine and Apoptotic Cell Death in Ornithine Decarboxylase Overproducing Mouse Myeloma Cells, Cell Growth & Differentiation, Oct. 1995, vol. 6, 1279-1285.
Tome et al., Excess putrescine accumulation inhibits the formation of modified eukaryotic initiation factor 5A (eIF-5A) and induces apoptosis, Biochem. J., (1997) 328, 847-854.
Tomlinson, I.M. et al. (Oct. 5, 1992). The Repertoire of Human Germline VHSequences Reveals About Fifty Groups of VH Segments with Different Hypervariable Loops, J. Mol. Biol., vol. 227, No. 3, pp. 776-798.
Traunecker, A. et al. (1991). Bispecific Single Chain Molecules (Janusins) Target Cytotoxic Lymphocytes on HIV Infected Cells, EMBO J., vol. 10, No. 12, pp. 3655-3659.
Tutt, A. et al. (Jul. 1, 1991). Trispecific F(ab')3 Derivatives That Use Cooperative Signaling via The TCR/CD3 Complex and CD2 to Activate and Redirect Resting Cytotoxic T Cells, J. Immunol., vol. 147, pp. 60-69.
Urlaub, G. et al. (Jul. 1980). Isolation of Chinese Hamster Cell Mutants Deficient in Dihydrofolate Reductase Activity, Proc. Natl. Acad. Sci. USA, vol. 77, No. 7, pp. 4216-4220.
Van Den Berg, J.A. (Feb. 1990). Kluyveromyces As A Host For Heterologous Gene Expression: Expression and Secretion of Prochymosin, Bio/Technology, vol. 8, pp. 135-139.
Verhoeyen, M. et al. (Mar. 25, 1988). Reshaping Human Antibodies: Grafting an Antilysozyme Activity, Science, vol. 239, pp. 1534-1536.
Vijayasankaran, N. et al. (2005). Synthesis of poly[(R)-3-hydroxybutyric acid) in the cytoplasm of Pichia pastoris under oxygen limitation, Biomacromolecules, vol. 6, pp. 604-611.
Vollmers, H.P. et al. (2005). The early birds: Natural IgM Antibodies and Immune Surveillance, Histology and Histopathology, vol. 20, No. 3, pp. 927-937.
Graham, T.L. et al. (1977). "Characteristics of a Human Cell Line Transformed by DNA From Human Adenovirus Type 5," J. Gen. Virol., vol. 36, pp. 59-72.
Gram H. et al. (Apr. 15, 1992). "In Vitro Selection and Affinity Maturations of Antibodies From a Naive Combinatorial Immunoglobulin Library," Proc. Natl. Acad. Sci. USA, vol. 89, pp. 3576-3580.
Griffiths, A.O. et al. (1993). "Human Anti-Self Antibodies with High Specificity From Phage Display Libraries," EMBO J., vol. 12, No. 2, pp. 725-734.
Gruber, M. et al. (1994). "Efficient Tumor Cell Lysis Mediated by a Bispecific Single Chain Antibody Expressed in *Escherichia coli*," J. Immunol., vol. 152, pp. 5368-5374.
Guirard et al., "Effect of polyamine structure on growth stimulation and spermine and spermidine content of lactic acid bacteria," Journal of Bacteriology, vol. 88, No. 1, p. 72-80, Jul. 1964.
Gürer, H. et al., "Antioxidant Effect of Taurine Against Lead-Induced Oxidative Stress" Archives of Environmental Contamination and Toxicology (2001) vol. 41, pp. 397-402.

Guss, B. et al. (1986). "Structure of the IgG-Binding Regions of Streptococcal Protein G," EMBO J., vol. 5, No. 7, pp. 1567-1575.
Ham, "Clonal Growth of Mammalian Cells in a Chemically Defined, Synthetic Medium," Nat'l Acad. Sci. USA, 1965, 53, pp. 288-293.
Ham, R.G. et al. (1979). "Media and Growth Requirement," Chapter 5 In Methods in Enzymology, Academic Press, Inc., vol. 58, pp. 44-93.
Hammerling, G.J. et al. Eds. (1981). "Monoclonal Antibodies and T-Cell Hybridomas," Chapter 12 In Research Monographs in Immunology Elsevier: New York, NY, vol. 3, pp. 563-681.
Han et al., "Effects of polyamines on apoptosis induced by simulated ischemia/reperfusion injury in cultured neonatal rat cardiomyocytes," Cell Biology International 31 (2007) 1345-1352.
Hawel, L. et al., "Selective putrescine export is regulated by insulin and ornithine in Reuber H35 hepatoma cells," Biochimica et Biophysica Acta, vol. 1222, No. 1, pp. 15-26, May 1994.
Hawkins, R.E. et al. (1992). "Selection of Phage Antibodies by Binding Affinity: Mimicking Affinity Maturation," J. Mol. Biol., vol. 226, pp. 889-896.
Hernández-Benítez et al., "Taurine Stimulates Proliferation of Mice Embryonic Cultured Neural Progenitor Cells," J Neurosci. Res., 2010, 88:1673-1681.
Hogrefe, H.H. et al. (Jun. 15, 1993). "A Bacteriophage Lambda Vector for the Cloning and Expression of Immunoglobulin Fab Fragments on the Surface of Filamentous Phage," Gene 128(1):119-126.
Hollenbaugh et al., "Construction of Immunoglobulin Fusion Proteins," Current Protocols in Immunology (2002), Supplement 48, Unit 10.19A, pp. 10.19A. 1-10.19A. 11.
Holliger, P. et al. (Jul. 1993). "Diabodies': Small Bivalent and Bispecific Antibody Fragments," Proc. Natl. Acad. Sci. USA, vol. 90, pp. 6444-6448.
Holmes et al., "Serum Fractionation and the Effects of Bovine Serum Fractions on Human Cells Grown in a Chemically Defined Medium," Biochem. Cytol., 1961, 10, pp. 389-401.
Holtta, E. et al., "Polyamine dependence of Chinese hamster ovary cells in serum-free culture is due to deficient arginase activity," Biochimica et Biophysica Acta, vol. 721, No. 4, pp. 321-327, Dec. 1982.
Hongo, J.-A.S et al. (1995). "Development and Characterization of Murine Monoclonal Antibodies to the Latency-Associated Peptide of Transforming Growth Factor β1," Hybridoma, vol. 14, No. 3, pp. 253-260.
Hoogenboom, H.R. et al. (1991). "Multi-Subunit Proteins on the Surface of Filamentous Phage: Methodologies for Displaying Antibody (Fab) Heavy and Light Chains," Nucl. Acids Res., vol. 19, No. 15, pp. 4133-4137.
Hoogenboom, H.R. et al. (1992). "By-Passing Immunisation: Human Antibodies From Synthetic Repertoires of Germline VH Gene Segments Rearranged in Vitro," J. Mol Biol., vol. 227, pp. 381-388.
Huang et al., "Maximizing Productivity of CHO Cell-Based Fed-Balch Culture Using Chemically Defined Media Conditions and Typical Manufacturing Equipment," Biotechnol. Prog., Sep.-Oct. 2010, 26(5), pp. 1400-1410.
Hudson, P.J. et al. (Jan. 2003). "Engineered Antibodies," Nat. Med., vol. 9, No. 1, pp. 129-134.
Igarashi, K. et al., "Modulation of cellular function by polyamines," International Journal of Biochemistry and Cell Biology, vol. 42, No. 1, pp. 39-51, Jan. 2010.
Jakobovits, A. et al. (Mar. 18, 1993). "Germ-line Transmission and Expression of a Human-Derived Yeast Artificial Chromosome," Nature, vol. 362, pp. 255-258.
Jakobovits, A. et al. (Mar. 1993). "Analysis of Homozygous Mutant Chimeric Mice: Deletion of the Immunoglobulin Heavy-Chain Joining Region Blocks B-Cell Development and Antibody Production," Proc. Natl. Acad. Sci. USA, vol. 90, pp. 2551-2555.
Jensen et al., "Selective inhibition of fibroblasts by spermine in primary cultures of normal human skin epithelial cells," In Vitro, vol. 18, No. 10, Oct. 1982, pp. 867-871.
Jones P.T. et al. (May 29, 1986). "Replacing the Complementarity-determining Regions in a Human Antibody With Those From a Mouse," Nature, vol. 321, pp. 522-525.

(56) References Cited

OTHER PUBLICATIONS

Jones, E.W. (Jan. 1977). "Proteinases Mutants of Saccharomyces cerevisiae," Genetics, vol. 85, pp. 23-33.
Jones, S.T. et al. (1991). "Rapid PCR-Cloning of Full-Length Mouse Immunoglobulin Variable Regions", Biotechnol., vol. 9, pp. 88-89.
Jong C. J. et al., "Mechanism Underlying the Antioxidant Activity of Taurine: Prevention of Mitochondrial Oxidant Production" Amino Acids (2012) vol. 42, pp. 2223-2232.
Jong, C. J. et al., "Effect of 13-Alanine Treatment on Mitochondrial Taurine Level and 5-Taurinomethyluridine Content" Journal of Biomedical Science (2010) vol. 17, Supplemental 1, S25, 7 pages total.
Jong, C. J. et al., "Role of Mitochondrial Permeability Transition in Taurine Deficiency-Induced Apoptosis" Exp. Clin. Cardiol. (2011) vol. 16, No. 4, pp. 125-128.
Kanemura et al., "In Vitro Screening of Exogenous Factors for Human Neural Stem/Progenitor Cell Proliferation Using Measurement of Total ATP Content in Viable Cells," Cell Transplantation, 2005, vol. 14, pp. 673-682.
Kang et al., "Metabolic markers associated with high mannose glycan levels of therapeutic recombinant monoclonal antibodies," Journal of Biotechnology (2015) 203: 22-31.
Kaufman et al., "Synthesis, Processing, and Secretion of Recombinant Human Factor VIII Expressed in Mammalian Cells," J. Biol. Chem., 1988, 263(13), pp. 6352-6362.
Kaufman, "Selection and Coamplification of Heterologous Genes in Mammalian Cells," Meth Enzymol, 1990, 185, pp. 537-566.
Kaufman, "Use of Recombinant DNA Technology for Engineering Mammalian Cells to Produce Proteins," Bioprocess Technology, 1990, vol. 10, pp. 15-69.
Allen et al., Inhibition of Lymphocyte Proliferation by Polyamines Requires Ruminant-Plasma Polyamine Oxidase, Eur. J. Biochem. 102, 153-158 (1979).
Altamirano et al., Analysis of CHO Cells Metabolic Redistribution in a Glutamate-Based Defined Medium in Continuous Culture, Biotechnol. Prog., Nov.-Dec. 2001, 17(6), pp. 1032-1041.
Altamirano et al., Specific nutrient supplementation of defined serum-free medium for the improvement of CHO cells growth and t-PA production, Electronic Journal of Biotechnology, Jan. 15, 2006, vol. 9 , No. 1, pp. 61-67.
Anonymous. (2000). U.S. Pharmacopoeia Inc., pp. 1926-1927.
Anonymous. (2008). European Pharmacopoeia 7th Ed., pp. 22-24.
Ashkenazi et al., Protection against endotoxic shock by a tumor necrosis factor receptor immunoadhesin, PNAS USA, Dec. 1991, 88:10535-10539.
Barbas, C.F. et al. (May 15, 1992). Semisynthetic Combinatorial Antibody Libraries: A Chemical Solution to the Diversity Problem, Proc. Natl. Acad. Sci. USA, vol. 89, No. 10, pp. 4457-4461.
Barbas, C.F. et al. (Sep. 1991). Assembly of Combinatorial Antibody Libraries on Phage Surfaces: The Gene III Site, Proc. Natl. Acad. Sci. USA, vol. 88, pp. 7978-7982.
Barnes, D. et al. (1980). Methods for Growth of Cultured Cells in Serum-Free Medium, Anal. Biochem., vol. 102, pp. 255-270.
CAS Registry No. 107-35-7, 2 pages, retrieved from https://www.commonchemistry.org/ChemicalDetail.aspx?ref=107-35-7.
Casero, Jr. and Marton, Targeting polyamine metabolism and function in cancer and other hyperproliferative diseases, Nature Reviews Drug Discovery, May 2007, vol. 6, pp. 373-390.
Vollmers, H.P. et al. (Apr. 2005). "Death by Stress: Natural IgM-Induced Apoptosis," Methods and Findings in Experimental and Clinical Pharmacology, vol. 27, No. 3, pp. 185-191.
Wahl and Holzgrabe, "Amino acid analysis for pharmacopoeial purposes," Talanta, Jul. 2016, 154:150-163.
Wang, X. et al. (Aug. 31, 2010). "New Approved Drugs in the World 2," Beijing: Chemical Industry Press, p. 252, with English Translation, 4 pages.
Ward, E.S. et al. (Oct. 12, 1989). "Binding Activities of a Repertoire of Single Immunoglobulin Variable Domains Secreted from *Escherichia coli*," Nature, vol. 341, pp. 544-546.
Waterhouse, P. et al. (1993). "Combinatorial Infection and in vivo Recombination: A Strategy for Making Large Phage Antibody Repertoires," Nucl. Acids Res., vol. 21, No. 9, pp. 2265-2266.
Williams et al., "Isolation and Long-Term Cell Culture of Epithelial-Like Cells From Rat Liver," Exp. Cell. Res., 1971, 69, pp. 106-112.
Williams, S.C. et al. (Jul. 1993). "Cloning and Sequencing of Human Immunoglobulin V Lambda Gene Segments," Eur. J. Immunol., vol. 23, No. 7, pp. 1456-1461.
Winter, G. et al. (1994). "Making Antibodies by Phage Display Technology," Ann. Rev. Immunol., vol. 12, pp. 433-455.
Wood et al., "High Level Synthesis of Immunoglobulins in Chinese Hamster Ovary Cells," J. Immuno., 1990, 145(9), pp. 3011-3016.
Yanagita et al., "Taurine reduces the Secretion of Apolipoprotein B100 and Lipids in HepG2 Cell," Lipids in Health and Disease (2008) vol. 7, No. 38, 6 pages.
Yaniv, J.M. (May 6, 1982). "Enhancing Elements for Activation of Eukaryotic Promoters," Nature, vol. 297, pp. 17-18.
Yazaki et al., "Expression of Recombinant Antibodies in Mammalian Cell Lines," Methods in Molecular Biology B.K.C.LO, ed. Human Press: Totowa, N.J. (2003) vol. 248, pp. 255-268.
Chen, Z et al. "A serum-free medium for hybridoma cell culture." Cytotechnology vol. 11,3 (1993): 169-74. doi: 10.1007/BF00749866.
Toyoda, K, and Inouye, I. "Development of a New Protein-and Hormone-free Medium for Hybridoma Cultivation." Agricultural and Biological Chemistry, vol. 55, 6, (1991):1631-1633, https://doi.org/10.1080/00021369.1991.10870806.
Lelong, I H, and G Rebel. "In vitro taurine uptake into cell culture influenced by using media with or without CO2." Journal of pharmacological and toxicological methods vol. 39,4 (1998): 211-20. doi:10.1016/s1056-8719(98)00020-3.

\* cited by examiner

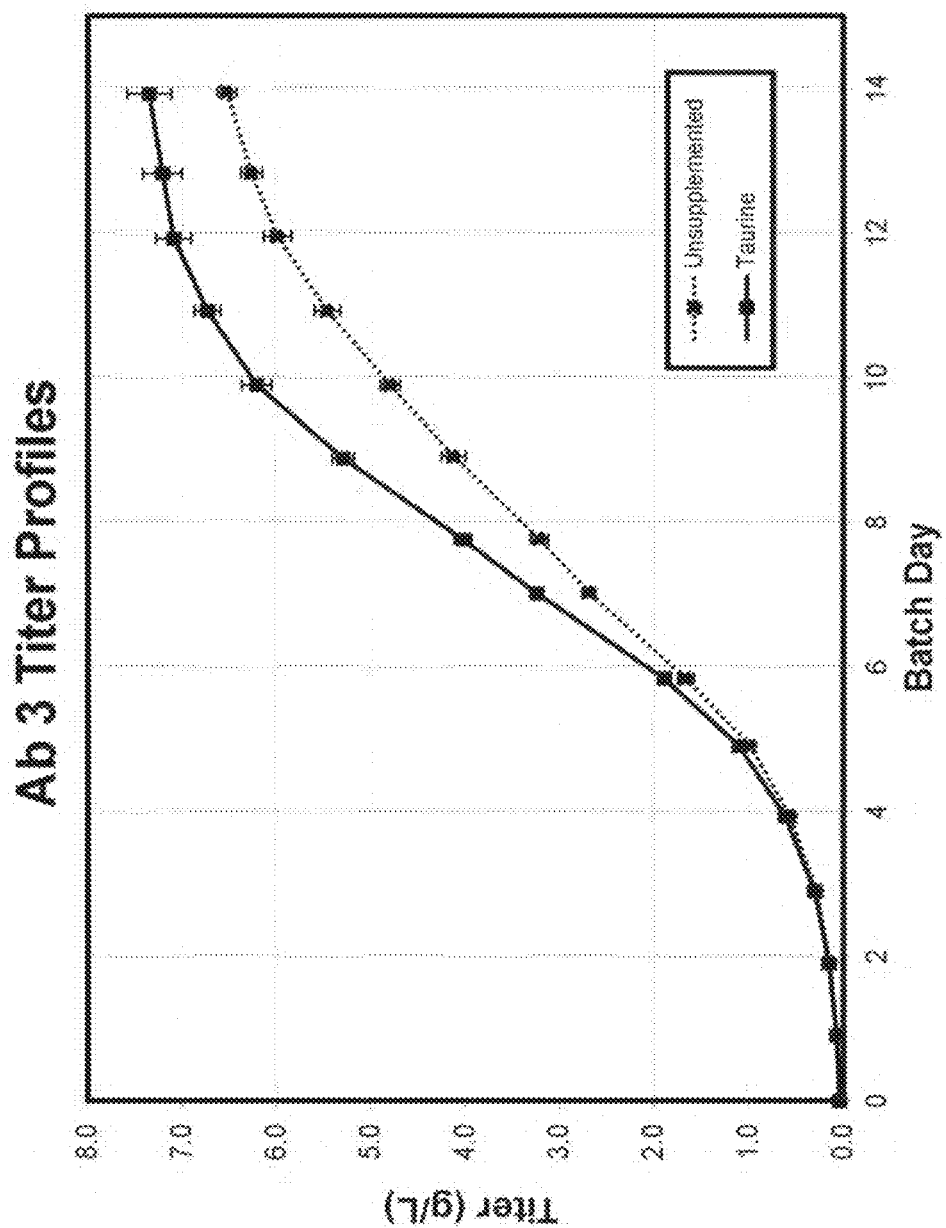

TAURINE SUPPLEMENTED CELL CULTURE MEDIUM AND METHODS OF USE

CROSS REFERENCE TO RELATED APPLICATIONS

This application is a continuation of U.S. application Ser. No. 18/371,959, filed Sep. 22, 2023, which is a continuation application of U.S. application Ser. No. 17/707,017, filed Mar. 29, 2022, which is a continuation of U.S. application Ser. No. 15/749,037, now U.S. Pat. No. 11,312,936, which is a national stage application filed under 35 U.S.C. § 371 of International Application No. PCT/US2016/045403, filed Aug. 3, 2016, which claims priority to and the benefit of U.S. Provisional Patent Application No. 62/200,689, filed Aug. 4, 2015, the contents of each of which are herein incorporated by reference in their entireties.

FIELD

The invention relates to medium and methods for the culturing of cells and for the production of recombinant proteins. The invention specifically relates to taurine supplemented medium and methods thereof for the culturing of recombinant eukaryotic cells for the production of protein biotherapeutics.

BACKGROUND

The organic acid taurine, often called a β-amino acid, is found in high concentrations in most
    tissues and is a derivative of the amino acid cysteine (Huxtable, R J., 1992, *Physiol Rev,* 72:101-163).

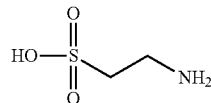

Structure of Taurine

Taurine is present in many tissues of humans and other mammalian species, e.g. brain, retina, myocardium, skeletal and smooth muscle, platelets and neutrophils. Taurine is recognized in helping osmoregulation, membrane stabilization and anti-inflammation, and also regulates mitochondrial protein synthesis through enhanced electron transport chain activity that protects against superoxide generation (Jong et al., 2010, *Journal of Biomedical Science* 17(Suppl 1):S25; Jong et al., 2012, *Amino Acids* 42:2223-2232sw). In primary neuronal cultures, taurine has been characterized as a cytoprotectant, due to its suppression of glutamate-induced toxicity. Various media for embryo culture have been developed containing taurine.

Cell culture techniques comprising amino acid feeds have a long history of use in the production of recombinant proteins from cultured cells. Amino acids are biosynthetic precursors, energy sources, osmolytes and the like, and their use in production cultures strongly correlates with continuous cell growth and productivity.

However, the physiological events that contribute to productivity and high yield protein expression are innumerable, and competing metabolic activities and transport mechanisms make the design of feeding strategies a challenge. The type of amino acid supplementation and timing of addition could also have an impact on the quality of the protein produced in culture (Altamirano, et al., 2006, *Electron. J Biotechnol.* 9:61-67). Accumulation of by-products is often problematic in production cell culture, and is considered a consequence of unbalanced nutrients in cell culture, ultimately inhibiting cell growth (Fan, Y. et al. *Biotechnol Bioeng.* 2015 March; 112(3):521-35). Hypotaurine or an analog or precursor thereof has been suggested in cell culture in order to achieve the desired results of reduced color intensity of a composition comprising a recombinantly produced polypeptide (WO2014145098A1, published 18 Sep. 2014). Cell culture medium including taurine that promotes the maturation of immature retinal pigmented epithelium cells into mature retinal pigmented epithelium cells has also been described (WO2013184809A1, published 12 Dec. 2013). However, optimizing recombinant protein productivity in taurine-supplemented cultures has not been recognized in the art. Cell culture processes that increase the productivity of the recombinantly expressed proteins, while minimizing the output of potentially toxic cell metabolism byproducts, such as ammonia, are highly desirable. Any consistent gain in productivity can equate to significantly higher supply at commercial scale of a biotherapeutic product.

Thus, there is a need in the art for medium and methods for culturing mammalian cells, wherein the medium allows for healthy and robust cell growth and maintenance, and high-titer production of biopharmaceutical drug substance.

SUMMARY

The inventors have made the surprising discovery that the inclusion of taurine in a cell culture medium increases cellular specific productivity and allows for lower ammonia byproduct by those cells. Various feeding strategies including taurine permit increased titer protein production. Furthermore, the addition of taurine has no negative impacts on culture performance or resulting antibody quality, The present invention provides a method for producing therapeutic protein in high yield comprising culturing a recombinant cell line in medium containing taurine, wherein the cell line comprises a stably integrated nucleic acid encoding the therapeutic protein.

The present invention relates to a cell culture medium, which is serum-free and comprises about 0.1 mM to about 10 mM taurine. The present invention relates to a cell culture medium, which is serum-free and comprises about 0.1 mM to about 1 mM taurine, about 0.2 to about 1 mM taurine, about 0.3 to about 1 mM taurine, about 0.4 to about 1 mM taurine, or about 0.5 to about 1 mM taurine. The present invention relates to a cell culture medium, which is serum-free and comprises about 1 mM to about 10 mM taurine. The present invention relates to a cell culture medium, which is serum-free and comprises about 1 mM to about 5 mM taurine, about 1 mM to about 6 mM taurine, about 1 mM to about 7 mM taurine, about 1 mM to about 8 mM taurine, or about 1 mM to about 9 mM taurine.

In some embodiments, the medium further comprises additional amino acids selected from the group consisting of arginine, histidine, lysine, aspartic acid, glutamic acid, serine, threonine, asparagine, glutamine, cysteine, glycine, proline, alanine, valine, isoleucine, leucine, methionine, phenylalanine, tyrosine, and tryptophan.

In some embodiments, the medium contains ≤16 g/L hydrolysate. In some embodiments, the medium is free of any hydrolysate.

In one embodiment, the medium contains a base medium that is chemically defined, such as a custom formulation or a commercially available base medium. In one embodiment, the complete medium is chemically defined, free of sera and free of hydrolysate.

In some embodiments, the total process including the base medium and feeds, contains a total of at least 115 mM of a mixture of amino acids or amino acid salts. In one embodiment, the mixture of amino acids comprises amino acids selected from the group consisting of arginine, histidine, lysine, aspartic acid, glutamic acid, serine, threonine, asparagine, glutamine, cysteine, glycine, proline, alanine, valine, isoleucine, leucine, methionine, phenylalanine, tyrosine, and tryptophan, in an amount selected from Table 1.

In some embodiments, the medium contains one or more fatty acids. In one particular embodiment, the medium contains a mixture of fatty acids (or fatty acid derivatives) and alpha tocopherol. Fatty acids or fatty acid derivatives are selected from the group consisting of linoleic acid, linolenic acid, thioctic acid, oleic acid. palmitic acid, stearic acid, arachidic acid, arachidonic acid, lauric acid, behenic acid, decanoic acid, dodecanoic acid, hexanoic acid, lignoceric acid, myristic acid, and octanoic acid.

In some embodiments, the medium contains a mixture of nucleosides. In one embodiment, the medium contains adenosine, guanosine, cytidine, uridine, thymidine, and hypoxanthine.

In some embodiments, the medium contains a mixture of salts. Salts include divalent cations, such as calcium and magnesium. In one embodiment, the medium contains calcium chloride and magnesium sulfate. Other salts may include those of phosphate.

In one embodiment, the medium (1) contains 0.1 f 0.015 mM, 1±0.015 mM, 3±0.05 mM, 5±0.10 mM, 7±0.15 mM, or 10±0.2 mM taurine, (2) contains ≤16 g/L of a hydrolysate, (3) is serum-free, (4) optionally additionally contains a mixture of amino acids, (5) contains a mixture of fatty acids, (6) contains a mixture of nucleosides including adenosine, guanosine, cytidine, uridine, thymidine, and hypoxanthine, and (7) contains salts of calcium, magnesium, and phosphate.

The present invention provides a method for producing a protein of interest in high yield comprising culturing a recombinant cell line in a cell culture medium containing at least about 0.1 mM to about 10 mM taurine, wherein the cell line comprises a stably integrated nucleic acid encoding the protein. In other embodiments, the medium embodies any of the foregoing aspects of the invention.

In another aspect, the invention provides a method for culturing eukaryotic cells for improved recombinant protein production, comprising the steps of: (a) propagating or maintaining cells in a defined cell culture medium during growth phase, (b) supplementing the base cell culture medium with about 0.1 mM to about 10 mM L-taurine and expressing a recombinant protein of interest during production phase, and (c) increasing titer of the protein of interest by the addition of taurine. In some embodiments, the taurine supplement is provided at least once during production phase, or twice, three times, four times, or five times during production phase, or on each day for the duration of the production phase. In other embodiments, the method further comprises supplementing the culture medium with about 0.1 mM to about 10 mM L-taurine during growth phase. In some embodiments, the method provides improved production of recombinant protein compared to a eukaryotic cells lacking taurine supplementation, or with less than 0.1 mM taurine supplementation and under otherwise identical conditions.

In another aspect, the invention provides a method for cultivating cells in a cell culture medium, such as any embodiment of the medium described in the foregoing aspect. In one embodiment, the method employs the steps of propagating or maintaining a cell or cells in a medium that (1) contains taurine at a concentration of at least 0.1 mM±0.015 mM, (2) contains s 16 g/L hydrolysate, or no hydrolysate, (3) is free of sera, (4) and optionally amino acids selected from the group consisting of a mixture of amino acids selected from Table 1.

In one embodiment, the optional mixture of amino acid supplements are selected from the group consisting of the amino acids in Table 1:

TABLE 1

| Amino acid | RANGE mM (mmol/L) | RANGE (g/L) |
|---|---|---|
| Alanine | 0-11.2 | 0-1 |
| Arginine | 2.4-11.9 | 0.5-2.5 |
| Asparagine | 1.3-33.3 | 0.2-5 |
| Aspartic Acid | 1.5-93.9 | 0.2-12.5 |
| Cysteine | 1.1-19.9 | 0.2-3.5 |
| Glutamic acid | 1.4-47.6 | 0.2-7 |
| Glutamine | 0-23.9 | 0-3.5 |
| Glycine | 0-16.7 | 0-1.25 |
| Histidine | 1-9.5 | 0.2-2 |
| Isoleucine | 1.5-22.9 | 0.2-3 |
| Leucine | 1.5-38.1 | 0.2-5 |
| Lysine | 2.7-24.6 | 0.5-4.5 |
| Methionine | 1.3-13.4 | 0.2-2 |
| Phenylalanine | 1.2-18.2 | 0.2-3 |
| Proline | 1.7-26.1 | 0.2-3 |
| Serine | 1.9-57.1 | 0.2-6 |
| Threonine | 1.7-33.6 | 0.2-4 |
| Tryptophan | 0.5-14.7 | 0.1-3 |
| Tyrosine | 0.9-22.2 | 0.2-5 |
| Valine | 1.7-34.1 | 0.2-4 |

In some embodiments, the cell or cells are mammalian cells, avian cells, insect cells, yeast cells, or bacteria cells. In one embodiment, the cells are mammalian cells useful in the production of recombinant proteins, such as CHO cells or the derivative CHO-K1. In some embodiments, the cells express a protein of interest, such as a biotherapeutic protein. The biotherapeutic protein may be an antigen binding protein, which may contain an Fc domain. In some embodiments, the protein of interest is an Fc-fusion protein, such as a ScFv molecule or a trap molecule. Trap molecules include, but are not limited to, the VEGF trap and IL-1 Trap proteins. In some embodiments, the protein of interest is an antibody, such as a human monoclonal antibody, humanized monoclonal antibody, a bispecific antibody, or an antibody fragment.

Given the positive effects on protein production by including taurine in various forms of serum-free media, the cells cultured according to this method result in an average increase in protein titer. In one embodiment, when compared to protein titer in a medium that has not been supplemented with taurine, the cells grown in taurine supplemented culture according to this method produce proteins having a protein titer that is at least 8% greater than the titer of the comparator control culture (i.e. culture that has not been supplemented with taurine). In one embodiment, the cells grown in taurine supplemented culture when compared to protein titer in media that has not been supplemented with taurine yield a protein titer that is at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, or at least 29% greater than the titer of the comparator control culture.

Likewise, the inclusion of taurine alone in serum-free media allows cultured cells to attain lower ammonia byproduct than without the inclusion of taurine. In one serum-free and hydrolysate-free embodiment of the taurine supplemented medium, the cell culture is capable of attaining a reduced ammonia byproduct level (mM $NH_3$) that is at least 4% lower, up to 32% lower than a similar cell culture in a similar cell culture medium that contains no supplementation (i.e. less than 0.1 mM taurine or no taurine supplement).

In another embodiment, the method includes the step of adding one or more point-of-use additions to the cell culture medium. In some embodiments, the point-of-use addition is any one or more of $NaHCO_3$, glutamine, insulin, glucose, $CuSO_4$, $ZnSO_4$, $NiSO_4$, $Na_4EDTA$, and $Na_3$ Citrate. In one embodiment, the method employs the step of adding each of the following point-of-use chemicals to the cell culture medium: $NaHCO_3$, glutamine, insulin, glucose, $CuSO_4$, $ZnSO_4$, $FeCl_3$, $NiSO_4$, $Na_4EDTA$, and $Na_3$ Citrate. In some embodiments, the point-of-use additions can be included in the medium at the outset.

In a specific embodiment, the aspect provides a method for cultivating cells in a serum-free medium consisting essentially of (1) taurine at a concentration of at least 0.1 mM; (2) contains≤16 g/L of a hydrolysate, (3) is serum-free, and (4) optionally additionally contains at least about 20 mM, or at least about 25 mM, or at least about 30 mM, or at least about 40 mM, or at least about 50 mM, or at least about 60 mM, or at least about 70 mM total of a mixture of amino acids selected from the group consisting of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

In another aspect, the invention provides a method for producing a protein of interest by employing the steps of (1) introducing into a cell a nucleic acid sequence that encodes a protein of interest; (2) selecting a cell or cells expressing the protein of interest: (3) culturing the selected cell in an embodiment of the serum-free cell culture medium described in any preceding aspect or according to any embodiment of the method described herein; and (4) expressing the protein of interest in the cell, wherein the protein of interest is secreted into the medium. In some embodiments, the cell used in the production of the protein is a mammalian cell capable of producing a biotherapeutic, such as CHO, 293, and BHK cell, or any derivatives of them. In one embodiment, the cell is a CHO cell, such as a CHO-K1 cell.

In some embodiments the protein of interest is an antigen binding protein. In some embodiments, the protein of interest is a protein that has an Fc domain. In some cases, those two proteins of interest may overlap, such as in the case of a receptor-Fc-fusion protein, an antibody, and a ScFv protein for example. Thus, in some embodiments, the protein of interest is an antibody, such as a human antibody or a humanized antibody, an antibody fragment, such as an Fab or $F(ab')_2$, a bispecific antibody, a trap molecule, such as a VEGF-Trap or an IL-1-Trap, an ScFv molecule, a soluble TCR-Fc fusion protein, or the like.

In one embodiment, the protein of interest is capable of being produced at an average 14, 15, 16 or 17 day titer that is at least 8% greater than the average 14, 15, 16 or 17 day titer produced by a similar cell in a serum-free cell culture medium that contains less than 0.1 mM or no taurine supplementation. In one embodiment, the protein of interest is capable of being produced at an average 6, 7, 8, 9, 10, 11, 12, 13, 14, 15, 16 or 17 day titer that is at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, or at least 29% greater than the average 6, 7, 8, 9, 10, 11, 12, 13, 14, 15, 16 or 17 day titer produced by a similar cell in a serum-free cell culture medium that contains less than 0.1 mM or no taurine supplementation.

In another embodiment, the protein of interest is produced by (1) introducing into a CHO cell a nucleic acid sequence that encodes a protein of interest, such as an antibody or other antigen-binding protein; (2) selecting a cell stably expressing the protein of interest; (3) culturing the selected cell in a serum-free cell culture medium comprising about 0.1 mM to about 10 mM taurine.

BRIEF DESCRIPTION OF THE DRAWINGS

The Figure shows the protein titer (yield) from samples retrieved at each day of production culture in an Ab3-producing cell culture, where taurine-supplementation is provided (solid squares connected by solid lines) compared to no taurine supplementation (x connected by dotted lines). The benefits of taurine-supplemented culture to protein yield can be seen as early as day 6 of the production culture.

DETAILED DESCRIPTION

It is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention is defined by the claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure.

Unless defined otherwise, all technical and scientific terms used herein have the same meaning as commonly understood by one of ordinary skill in the art to which this invention belongs. Although any methods and materials similar or equivalent to those described herein can be used in the practice of the present invention, particular methods and materials are now described. All publications mentioned herein are incorporated herein by reference in their entirety.

The applicants have made the surprising discovery that the addition of taurine to a cell culture medium improves protein production by a recombinant cell in a cell culture relative to a cell culture medium that contains very little or no taurine.

Before the present cell cultures and methods are described, it is to be understood that this invention is not limited to particular methods and experimental conditions described, as such methods and conditions may vary. It is also to be understood that the terminology used herein is for the purpose of describing particular embodiments only, and is not intended to be limiting.

The section headings used herein are for organizational purposes only and are not to be construed as limiting the subject matter described. The methods and techniques described herein are generally performed according to conventional methods known in the art and as described in various general and more specific references that are cited and discussed throughout the present specification unless otherwise indicated. See, e.g., Sambrook et al., Molecular Cloning: A Laboratory Manual, 3$^{rd}$ ed., Cold Spring Harbor Laboratory Press, Cold Spring Harbor, N. Y. (2001) and Ausubel et al., Current Protocols in Molecular Biology, Greene Publishing Associates (1992), Harlow and Lane Antibodies: A Laboratory Manual, Cold Spring Harbor Laboratory Press, Cold Spring Harbor, N.Y. (1990), and Julio E. Celis, Cell Biology: A Laboratory Handbook, 2$^{nd}$ ed., Academic Press, New York, N.Y. (1998), and Dieffenbach and Dveksler, PCR Primer: A Laboratory Manual, Cold Spring Harbor Laboratory Press, Cold Spring Harbor, N.Y. (1995). All publications mentioned throughout this disclosure are incorporated herein by reference in their entirety.

Definitions

"Taurine" is also known as 2-aminoethanesulfonic acid (IUPAC nomenclature; CAS Registry No. 107-35-7). "Taurine" and "L-taurine" are used interchangeably to refer to the same organic compound. Taurine is an organic acid containing an amino group, however is not considered an "amino acid" as traditionally known to those in the art, whereas amino acids contain both an amino group and a carboxyl group. Biosynthesis of taurine occurs when hypotaurine, which is a derivative of cysteine, is converted to taurine by oxidation.

The terms "supplementation", "supplementing", "supplemented with", and the like, refer to adding an ingredient, a component, a molecule, etc. which may be used in a medium for cell culture to maintain and/or promote the growth and/or differentiation of cells, to extend or strengthen an attribute of the culture or cells as a whole, or to make up for a deficiency. To this end, taurine-supplementation includes the addition of taurine at a particular concentration in a solution to the culture medium.

The terms "peptide," "polypeptide" and "protein" are used interchangeably throughout and refer to a molecule comprising two or more amino acid residues joined to each other by a peptide bond. Peptides, polypeptides and proteins may also include modifications such as glycosylation, lipid attachment, sulfation, gamma-carboxylation of glutamic acid residues, alkylation, hydroxylation and ADP-ribosylation. Peptides, polypeptides, and proteins can be of scientific or commercial interest, including protein-based drugs. Peptides, polypeptides, and proteins include, among other things, antibodies and chimeric or fusion proteins. Peptides, polypeptides, and proteins are produced by recombinant animal cell lines using cell culture methods.

The term "heterologous polynucleotide sequence", as used herein refers to nucleic acid polymers encoding proteins of interest, such as chimeric proteins (like trap molecules), antibodies or antibody portions (e.g., VH, VL, CDR3) that are produced as a biopharmaceutical drug substance. The heterologous polynucleotide sequence may be manufactured by genetic engineering techniques (e.g., such as a sequence encoding a chimeric protein, or a codon-optimized sequence, an intronless sequence, et cetera) and introduced into the cell, where it may reside as an episome or be intergrated into the genome of the cell. The heterologous polynucleotide sequence may be a naturally occurring sequence that is introduced into an ectopic site within the production cell genome. The heterologous polypeptide sequence may be a naturally occurring sequence from another organism, such as a sequence encoding a human ortholog.

"Antibody" refers to an immunoglobulin molecule consisting of four polypeptide chains, two heavy (H) chains and two light (L) chains inter-connected by disulfide bonds. Each heavy chain has a heavy chain variable region (HCVR or VH) and a heavy chain constant region. The heavy chain constant region contains three domains, CH1, CH2 and CH3. Each light chain has a light chain variable region and a light chain constant region. The light chain constant region consists of one domain (CL). The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The term "antibody" includes reference to both glycosylated and non-glycosylated immunoglobulins of any isotype or subclass. The term "antibody" includes antibody molecules prepared, expressed, created or isolated by recombinant means, such as antibodies isolated from a host cell transfected to express the antibody. The term antibody also includes bispecific antibody, which includes a heterotetrameric immunoglobulin that can bind to more than one different epitope. Bispecific antibodies are generally described in US Patent Application Publication No. 2010/0331527, which is incorporated by reference into this application.

The term "antigen-binding portion" of an antibody (or "antibody fragment"), refers to one or more fragments of an antibody that retain the ability to specifically bind to an antigen. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) Nature 241:544-546), which consists of a VH domain, (vi) an isolated CDR, and (vii) an scFv, which consists of the two domains of the Fv fragment, VL and VH, joined by a synthetic linker to form a single protein chain in which the VL and VH regions pair to form monovalent molecules. Other forms of single chain antibodies, such as diabodies are also encompassed under the term "antibody" (see e.g., Holliger et al. (1993) PNAS USA 90:6444-6448; Poljak et al. (1994) Structure 2:1121-1123).

Still further, an antibody or antigen-binding portion thereof may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov et al. (1995) Human Antibodies and Hybridomas 6:93-101) and use of a cysteine residue, a marker peptide and a C-terminal polyhistidine tag to make bivalent and biotinylated scFv molecules (Kipriyanov et al. (1994) Mol. Immunol. 31:1047-1058). Antibody portions, such as Fab and F(ab')2 fragments, can be prepared from whole antibodies using conventional techniques, such as via papain or pepsin digestion of whole antibodies. Moreover, antibodies, antibody portions and immunoadhesion molecules can be obtained using standard recombinant DNA techniques commonly known in the art (see Sambrook et al., 1989).

The term "human antibody" is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

"Fc fusion proteins" comprise part or all of two or more proteins, one of which is an Fc portion of an immunoglobulin molecule, which are not otherwise found together in nature. Preparation of fusion proteins comprising certain heterologous polypeptides fused to various portions of antibody-derived polypeptides (including the Fc domain) has been described, e.g., by Ashkenazi et al., Proc. Natl. Acad. ScL USA 88: 10535, 1991; Byrn et al., Nature 344:677, 1990; and Hollenbaugh et al., "Construction of Immunoglobulin Fusion Proteins", in Current Protocols in Immunology, Suppl. 4, pages 10.19.1-10.19.11, 1992. "Receptor Fc fusion proteins" comprise one or more extracellular domain(s) of a receptor coupled to an Fc moiety, which in some embodiments comprises a hinge region followed by a CH2 and CH3 domain of an immunoglobulin. In some embodiments, the Fc-fusion protein contains two or more distinct receptor chains that bind to a one or more ligand(s). For example, an Fc-fusion protein is a trap, such as for example an IL-1 trap (e.g., rilonacept, which contains the IL-IRAcP ligand binding region fused to the IL-1R1 extracellular region fused to Fc of hIgG1: see U.S. Pat. No. 6,927,004), or a VEGF trap (e.g., aflibercept, which contains the Ig domain 2 of the VEGF receptor Flt1 fused to the Ig domain 3 of the VEGF receptor Flk1 fused to Fc of hIgG1; see U.S. Pat. Nos. 7,087,411 and 7,279,159).

Cell Culture

The terms "cell culture medium" and "culture medium" refer to a nutrient solution used for growing mammalian cells that typically provides the necessary nutrients to enhance growth of the cells, such as a carbohydrate energy source, essential (e.g. phenylalanine, valine, threonine, tryptophan, methionine, leucine, isoleucine, lysine, and histidine) and nonessential (e.g. alanine, asparagine, aspartic acid, cysteine, glutamic acid, glutamine, glycine, proline, serine, and tyrosine) amino acids, trace elements, energy sources, lipids, vitamins, etc. Cell culture medium may contain extracts, e.g. serum or peptones (hydrolysates), which supply raw materials that support cell growth. Media may contain yeast-derived or soy extracts, instead of animal-derived extracts. Chemically defined medium refers to a cell culture medium in which all of the chemical components are known (i.e. have a known chemical structure). Chemically defined medium is entirely free of animal-derived components, such as serum- or animal-derived peptones. In one embodiment, the medium is a chemically defined medium.

The solution may also contain components that enhance growth and/or survival above the minimal rate, including hormones and growth factors. The solution is preferably formulated to a pH and salt concentration optimal for cell survival and proliferation.

A "cell line" refers to a cell or cells that are derived from a particular lineage through serial passaging or subculturing of cells. The term "cells" is used interchangeably with "cell population".

The term "cell" includes any cell that is suitable for expressing a recombinant nucleic acid sequence. Cells include those of eukaryotes, such as non-human animal cells, mammalian cells, human cells, avian cells, insect cells, yeast cells, or cell fusions such as, for example, hybridomas or quadromas. In certain embodiments, the cell is a human, monkey, ape, hamster, rat or mouse cell. In other embodiments, the cell is selected from the following cells: CHO (e.g. CHO K1, DXB-11 CHO, Veggie-CHO), COS (e.g. COS-7), retinal cell, Vero, CV1, kidney (e.g. HEK293, 293 EBNA, MSR 293, MDCK, HaK, BHK21), HeLa, HepG2, W138, MRC 5, Colo25, HB 8065, HL-60, lymphocyte, e.g. Jurkat (T lymphocyte) or Daudi (B lymphocyte), A431 (epidermal), CV-1, U937, 3T3, L cell, C127 cell, SP2/0, NS-0, MMT cell, stem cell, tumor cell, and a cell line derived from an aforementioned cell. In some embodiments, the cell comprises one or more viral genes, e.g. a retinal cell that expresses a viral gene (e.g. a PER.C6® cell). In some embodiments, the cell is a CHO cell. In other embodiments, the cell is a CHO K1 cell.

One aspect of the invention relates to a seed culture in which a cell population is expanded prior to protein production and harvest in the production culture. Taurine may be added to the base medium in a seed culture formulation, according with the invention as described herein.

Another aspect of the invention relates to a production culture in which protein is produced and harvested. Prior to production phase, there is typically a growth phase (also known as a seed train or seed culture) wherein all components for cell culturing are supplied to the culturing vessel at the start of the culturing process then cell population is expanded until ready for production scale. As such, the culturing vessel is inoculated with cells at a suitable seeding density for the initial cell growth phase depending on the starting cell line. In some aspects, taurine may be added to the basal culture medium in a seed culture formulation, according with the invention as described herein in order to further improve or enhance the productivity of the cells in the subsequent production phase.

One aspect of the invention relates to a production culture wherein cell culture conditions are modified to enhance the growth of recombinant eukaryotic cells while improving the production of one or more recombinant proteins of interest by such cells and maintaining cell viability, in particular by adding taurine to the production culture medium and/or the seed train culture. In the production culturing vessel or bioreactor, a basal culture medium and cells are supplied to a culturing vessel following a seed culture or growth phase. In certain embodiments, the cell supernatant or cell lysate is harvested following the production culture, In other embodiments, the polypeptide or protein of interest is recovered from the culture medium or cell lysate, or whatever the case may be depending on the location of the protein of interest, using techniques well known in the art Culturing vessels include, but are not limited to well plates, T-flasks, shake flasks, stirred vessels, spinner flasks, hollow fiber, air lift bioreactors, and the like. A suitable cell culturing vessel is a bioreactor. A bioreactor refers to any culturing vessel that is manufactured or engineered to manipulate or control environmental conditions. Such culturing vessels are well known in the art.

Bioreactor processes and systems have been developed to optimize gas exchange, to supply sufficient oxygen to sustain cell growth and productivity, and to remove $CO_2$. Maintaining the efficiency of gas exchange is an important criterion for ensuring successful scale up of cell culture and protein production. Such systems are well-known to the person having skill in the art.

In the polypeptide production phase, a "fed-batch cell culture" or "fed-batch culture" refers to a batch culture wherein the animal cells and culture medium are supplied to the culturing vessel initially and additional culture nutrients are slowly fed, continuously or in discrete increments, to the culture during culturing, with or without periodic cell and/or product harvest before termination of culture. Fed-batch culture includes "semi-continuous fed-batch culture" wherein periodically whole culture (which may include cells and medium) is removed and replaced by fresh medium. Fed-batch culture is distinguished from simple "batch culture" whereas all components for cell culturing (including the animal cells and all culture nutrients) are supplied to the culturing vessel at the start of the culturing process in batch culture. Fed-batch culture can be further distinguished from perfusion culturing insofar as the supernatant is not removed from the culturing vessel during the process, whereas in perfusion culturing, the cells are restrained in the culture by, e.g., filtration, and the culture medium is continuously or intermittently introduced and removed from the culturing vessel. However, removal of samples for testing purposes during fed-batch cell culture is contemplated. The fed-batch process continues until it is determined that maximum working volume and/or protein production is reached.

The phrase "continuous cell culture" when used herein relates to a technique used to grow cells continually, usually in a particular growth phase. For example, if a constant supply of cells is required, or the production of a particular polypeptide or protein of interest is required, the cell culture may require maintenance in a particular phase of growth. Thus, the conditions must be continually monitored and adjusted accordingly in order to maintain the cells in that particular phase.

Media

The present invention provides a cell culture medium, which is serum-free, comprising about 0.1 mM to 10 mM taurine. "Serum-free" applies to a cell culture medium that does not contain animal sera, such as fetal bovine serum. The serum-free media may contain ≤16 g/L of hydrolysates, such as soy hydrolysate. The present invention also provides chemically defined media, which is not only serum-free, but also hydrolysate-free. "Hydrolysate-free" applies to cell culture media that contains no exogenous protein hydrolysates such as animal or plant protein hydrolysates such, for example peptones, tryptones and the like. "Base medium" is the initial medium (present in the seed train and/or at day 0 of the cell culture production) in which the cells are propagated and contains all the necessary nutrients, which includes a base mixture of amino acids. Various recipes (i.e. formulations) for base media may be manufactured or purchased in commercially available lots. Likewise "base feed medium" contains mixtures of supplemental nutrients that are commonly consumed during a production culture and are utilized in a feeding strategy (for a so-called "fed-batch" culture). Varieties of base feed media are commercially available. A "feed" includes scheduled additions or additions to media at regular intervals, such as according to a protocol, including a continuous feed culture system, as in a chemostat (see C. Altamirano et al., Biotechnol Prog. 2001 November-December: 17(6):1032-41), or according to a fed-batch process (Y. M. Huang et al., Biotechnol Prog. 2010 September-October; 26(5): 1400-10). For example, a culture may be fed once per day, every other day, every three days, or may be fed when the concentration of a specific medium component, which is being monitored, falls outside a desired range.

The elimination of serum and reducing or eliminating hydrolysates from cell culture media, while reducing lot-to-lot variability and enhancing downstream processing steps, unfortunately diminishes cell growth, viability and protein expression Thus, chemically defined serum-free and low to no hydrolysate media requires additional ingredients to improve cell growth and protein production.

Thus, the cell culture medium of the invention comprises a base medium containing all necessary nutrients for a viable cell culture. Taurine may be added to the base medium in a seed culture formulation, according with the invention as described herein. Furthermore, taurine may be added to the base medium in a production culture formulation, which may then be fed periodically (as in so-called "fed-batch" cultures) with or without additional ingredients such as polyamines or increased concentrations of components like amino acids, salts, sugars, vitamins, hormones, growth factors, buffers, antibiotics, lipids, trace elements and the like, depending on the requirements of the cells to be cultured or the desired cell culture parameters.

The invention provides that the taurine-supplemented cell culture medium may be depleted of amino acids over the course of the protein production culture, where no additional amino acid supplementation is provided, or the taurine-supplemented cell culture medium may be "non-depleted", where amino acid supplementation is provided for the depleted amino acids (as described below). The inventors have observed that cultures supplemented during production phase with taurine improve recombinant protein production under various culture conditions as described in the foregoing.

The invention provides taurine-supplemented medium which contains taurine at a concentration (expressed in millimoles per liter) of at least about 0.1, 0.2, 0.3, 0.4, 0.5, 0.6, 0.7, 0.8, 0.9, 1, 2, 3, 4, 5, 6, 7, 8, 9 or 10 mM.

In one embodiment, the medium additionally contains 100 pM±15 pM ornithine, or 300 pM±45 pM ornithine, or 600 pM±90 pM ornithine, or even 900 pM 135 pM ornithine. In another embodiment, the medium contains at least about 5 mg/L±1 mg/L ornithine·HCl, or at least about, 10 mg/L±2 mg/L ornithine·HCl, 15 mg/L±2.25 mg/L ornithine·HCl, or at least about 50 mg/L±7.5 mg/L ornithine·HCl, or at least about 100 mg/L±15 mg/L ornithine·HCl, or at least about 150 mg/L±22.5 mg/L ornithine·HCl.

Putrescine may optionally be added to the supplemented media. Putrescine has been included, at very low concentrations, as a component in some cell culture media formulations; see for example WO 2005/028626, which describes 0.02-0.08 mg/L putrescine; U.S. Pat. No. 5,426,699 (0.08 mg/L); U.S. Pat. No. RE30,985 (0.16 mg/L); U.S. Pat. No. 5,811,299 (0.27 mg/L); U.S. Pat. No. 5,122,469 (0.5635 mg/L); U.S. Pat. No. 5,063,157 (1 mg/L); WO 2008/154014 (~100 pM-1000 pM); US Pat. App. No. 2007/0212770 (0.5-30 mg/L polyamine; 2 mg/L putrescine; 2 mg/L putrescine+2 mg/L ornithine; 2 mg/L putrescine+10 mg/L ornithine).

In some embodiments, the media is further supplemented with a combination of ornithine and putrescine, wherein the putrescine can be at a concentration of at least about 150 to 720 µM. In some embodiments, the media is further supplemented with putrescine at a concentration of about 170 to 230 µM. In one embodiment, the medium contains 200 µM±30 µM putrescine in addition to ≥90 µM±15 µM ornithine. In one embodiment, the medium contains s 30 mg/L±4.5 mg/L putrescine·2HCI in addition to s 15 mg/L±2.25 mg/L ornithine. In another embodiment, the medium contains ≥30 mg/L±4.5 mg/L putrescine·2HCI in addition to ≥15 mg/L±2.25 mg/L ornithine·HCl. (See International Publication No. WO2014/144198A1, published on Sep. 18, 2014, which is herein incorporated by reference in its entirety.)

In still other embodiments, ornithine is present in the medium at a concentration ranging from 0.09±0.014 mM to 0.9±0.14 mM, such as 0.09±0.014 mM, 0.3±0.05 mM, 0.6±0.09 mM, or 0.9±0.14 mM ornithine. In some embodiments, the medium also contains at least 0.20±0.03 mM putrescine. In some embodiments, the additional putrescine is at a concentration ranging from 0.20±0.03 mM to 0.714±0.11 mM, such as 0.20±0.03 mM, 0.35±0.06, or 0.714±0.11 mM putrescine.

Various other supplements may be added to the culture medium, and are within the skill of the person in the art to determine additionally appropriate conditions. In some embodiments, the medium is supplemented with a mixture of amino acids selected from the group consisting of aspartic acid, cysteine, glutamic acid, glycine, lysine, phenylalanine, proline, serine, threonine, valine, arginine, histidine, asparagine, glutamine, alanine, isoleucine, leucine, methionine, tyrosine, and tryptophan, in order to be non-depleted or as supplemental nutrients are needed.

In one embodiment, the media is further supplemented with about 170 µM to 175 µM nucleosides. In one embodiment, the media contains purine derivatives in a cumulative concentration of at least 40 µM, at least 45 µM, at least 50 µM, at least 55 µM, at least 60 µM, at least 65 µM, at least 70 µM, at least 75 µM, at least 80 µM, at least 85 µM, at least 90 µM, at least 95 µM, at least 100 µM, or at least 105 µM. In one embodiment, the media contains about 100 µM to 110 µM of purine derivatives. Purine derivatives include hypoxanthine and the nucleosides adenosine and guanosine. In one embodiment, the media contains pyrimidine derivatives in a cumulative concentration of at least 30 µM, at least 35 µM, at least 40 µM, at least 45 µM, at least 50 µM, at least 55 µM, at least 60 µM, or at least 65 µM. In one embodiment, the media contains about 65 µM to 75 µM of pyrimidine derivatives. Pyrimidine derivatives include the nucleosides thymidine, uridine, and cytidine. In one particular embodiment, the media contains adenosine, guanosine, cytidine, uridine, thymidine and hypoxanthine.

In addition to the inclusion of any of the above additives, in one embodiment, the media is further supplemented with micromolar amounts of fatty acids (or fatty acid derivatives) and tocopherol In one embodiment, the fatty acids include any one or more of linoleic acid, linolenic acid, thioctic acid, oleic acid, palmitic acid, stearic acid, arachidic acid, arachidonic acid, lauric acid, behenic acid, decanoic acid, dodecanoic acid, hexanoic acid, lignoceric acid, myristic acid, and octanoic acid. In one embodiment, the media contains tocopherol, linoleic acid, and thioctic acid.

In one embodiment, the media also may be further supplemented with a mixture of vitamins, which includes other nutrients and essential nutrients, at a cumulative concentration of at least about 700 µM or at least about 2 mM. In one embodiment, the mixture of vitamins contains one or more of D-biotin, choline chloride, folic acid, myo-inositol, niacinamide, pyridoxine HCI, D-pantothenic acid (hemiCa), riboflavin, thiamine HCI, vitamin B12, and the like. In one embodiment, the mixture of vitamins includes all of D-biotin, choline chloride, folic acid, myo-inositol, niacinamide, pyridoxine HCI, D-pantothenic acid (hemiCa), riboflavin, thiamine HCI, and vitamin B12.

Various embodiments of the media of the invention include any of the combinations of the above described embodiments, including chemically defined, hydrolysate-free serum-free media comprising taurine in the indicated amounts, plus inter alia (a) amino acids: (b) optionally nucleosides; (c) salts of divalent cations; (d) fatty acids and tocopherol; and (e) vitamins. In some embodiments, all small amounts of hydrolysates may be added to the taurine-supplemented media.

The applicants envision that in the practice of this invention any one or more of a variety of base media or combinations thereof, to which the taurine may be used. Base media are generally known in the art and include inter alia Eagle's MEME (minimal essential media) (Eagle, Science, 1955, 112(3168):501-504), Ham's F12 (Ham, Proc. Nat'l. Acad. Sci. USA, 1965, 53:288-293), F-12 K medium, Dulbecco's medium, Dulbecco's Modified Eagle Medium (Proc. Natl. Acad. Sci. USA., 1952 August; 38(8): 747-752), DMEM/Ham's F12 1:1, Trowell's T8, A2 media Holmes and Wolf, Biophys. Biochem. Cytol., 1961, 10:389-401), Waymouth media (Davidson and Waymouth, Biochem. J., 1945, 39(2):188-199), Williams E media (William's et al., Exp. Cell Res., 1971, 69:105 et seq.), RPMI 1640 (Moore et al., J. Amer. Med. Assoc., 1967, 199:519-524), MCDB 104/110 media (Bettger et al., Proc. Nat'l. Acad. Sci. USA, 1981, 78(9):5588-5592), Ventrex HL-1 media, albumin-globulin media (Orr et al., Appl. Microbiol., 1973, 25(1): 49-54), RPMI-1640 Medium, RPMI-1641 Medium, Iscove's Modified Dulbecco's Medium, McCoy's 5 A Medium, Leibovitz's L-15 Medium, and serum-free media such as EXCELL™ 300 Series (JRH Biosciences, Lenexa, Kansas), protamine-zinc-insulin media (Weiss et al., 1974, U.S. Pat. No. 4,072,565), biotin-folate media (Cartaya, 1978, U.S. Re30,985), Transferrin-fatty acid media (Baker, 1982, U.S. Pat. No. 4,560,655), transferrin-EGF media (Hasegawa, 1982, U.S. Pat. No. 4,615,977; Chessebeuf, 1984, U.S. Pat. No. 4,786,599), and other media permutations (see Inlow, U.S. Pat. No. 6,048,728; Drapeau, U.S. Pat. No. 7,294,484; Mather, U.S. Pat. No. 5,122,469; Furukawa, U.S. Pat. No. 5,976,833; Chen, U.S. Pat. No. 6,180,401; Chen, U.S. Pat. No. 5,856,179; Etcheverry, U.S. Pat. No. 5,705,364; Etcheverry, U.S. Pat. No. 7,666,416; Ryll, U.S. Pat. No. 6,528,286; Singh, U.S. Pat. No. 6,924,124; Luan, U.S. Pat. No. 7,429,491; and the like).

In a particular embodiment, the media is chemically defined and contains in addition to the taurine: amino acid mixtures as defined herein, $CaCl_2$) $2H_2O$; HEPES buffer, KCl; $MgSO_4$; NaCl; $Na_2HPO_4$ or other phosphate salts; pyruvate; D-biotin; choline chloride; folic acid; myo-inositol; niacinamide; pyridoxine HCI; D-pantothenic acid; riboflavin; thiamine HCI; vitamin B12; p-aminobenzoic acid;

ethanolamine HCI; poloxamer 188; DL-a-tocopherol phosphate; linoleic acid; $Na_2SeO$; thioctic acid; and glucose; and optionally adenosine; guanosine; cytidine; uridine; thymidine; and hypoxanthine 2Na.

In one embodiment, the starting osmolarity of the media of the invention is 200-500, 250-400, 275-350, or about 300 mOsm. During growth of the cells in the media of the invention, and in particular following any feedings according to a fed batch protocol, the osmolarity of the culture may increase up to about 350, 400, 450, 500 or up to about 550 mOsm.

In some embodiments wherein the osmolarity of the defined medium is less than about 300, the osmolarity is brought to about 300 with the addition of one or more salts in excess of the amount specified. In one embodiment, osmolarity is increased to a desired level by adding one or more of an osmolyte selected from sodium chloride, potassium chloride, a magnesium salt, a calcium salt, an amino acid salt, a salt of a fatty acid, sodium bicarbonate, sodium carbonate, potassium carbonate, a chelator that is a salt, a sugar (e.g., galactose, glucose, sucrose, fructose, fucose, etc.), and a combination thereof. In one embodiment, the osmolyte is added over and above its concentration in a component already present in the defined medium (e.g., a sugar is added over and above the concentration specified for a sugar component).

Each and every embodiment of the media described above, as well as any other serum-free media containing at least about 0.1 mM taurine is referred to as taurine supplemented media. Conversely, media containing no taurine, or media containing less than 0.1 mM taurine, are hereinafter referred to as non-taurine supplemented media or no taurine supplementation.

Fed-Batch Culture

Feeding strategies for cell culture aim to ensure the optimal growth and propagation of cells outside of a multicellular organism or tissue. Suitable culture conditions for mammalian cells are known in the art. See e.g. Animal cell culture: A Practical Approach, D. Rickwood, ed., Oxford University Press, New York (1992). Mammalian cells may be cultured in suspension or while attached to a solid substrate. Fluidized bed bioreactors, hollow fiber bioreactors, roller bottles, shake flasks, or stirred tank bioreactors, with or without microcarriers, and operated in a batch, fed batch, continuous, semi-continuous, or perfusion mode are available for mammalian cell culture. Cell culture media or concentrated feed media may be added to the culture continuously or at intervals during the culture. For example, a culture may be fed once per day, every other day, every three days, or may be fed when the concentration of a specific medium component, which is being monitored, falls outside a desired range.

In addition to the inclusion of taurine, in one embodiment, media may be further supplemented with amino acids in a cumulative (total) concentration of at least 20 mM. In one embodiment, the concentration of initial amino acids included in the starting cell culture medium is not included in such cumulative (total) concentration of supplemented amino acids. In one embodiment of the cell culture medium, or in the method to culture cells or the method to produce a protein of interest, the media may be supplemented in an amount greater than about 20 mM, greater than about 25 mM, greater than about 30 mM, greater than about 40 mM greater than about 50 mM, or greater than about 60 mM, greater than about 70 mM, greater than about 100 mM, greater than about 200 mM, greater than about 300 mM, greater than about 400 mM, or greater than about 500 mM See also Table 1 herein. In one embodiment the amount of amino acids added to the media is about 30 mM±10 mM or more.

Supplemental feeding regimens may be optimized by those skilled in the art to support cell growth, minimize cell stress, or to provide a "non-depleted medium" during production phase.

"Non-depleted medium" includes cell culture medium that has been determined to have the nutrients, in particular, the amino acids necessary for production of a recombinant protein of interest. Amino acid feeds typically supplement the amino acids needed as building blocks for producing a recombinant protein in a cell culture. However, some amino acids may be depleted faster than others depending on the requirements of that particular protein produced by the cells in culture. In a non-depleted medium, the feeding regime has been determined such that necessary amino acids are replenished as they are consumed. Thus, depletion and subsequently optimal consumption rates (pg/cell-day) may be determined by the following steps: culturing eukaryotic cell(s) expressing the protein of interest in a cell culture medium; measuring each amino acid concentration in the culture medium at time points to establish a depletion level; identifying the depletion time point at which the amino acid concentration falls below the depletion level; calculating consumption rates for each amino acid; and determining the optimal consumption rate as the consumption rate at the time point immediately prior to the depletion time point. The cell culture is then supplemented with an appropriate concentration of a particular amino acid to maintain such optimal consumption rates as determined, in order for the culture medium to be non-depleted.

It is understood that the present invention provides a taurine-supplemented cell culture medium that improves protein titer in depleted, as well as non-depleted, cultures.

The present invention provides a cell culture comprising a cell line expressing a protein of interest in a taurine-supplemented medium as described above. Examples of cell lines that are routinely used to produce protein biotherapeutics include inter alia primary cells. BSC cells, HeLa cells, HepG2 cells, LLC-MK cells, CV-1 cells, COS cells, VERO cells, MDBK cells, MDCK cells, CRFK cells, RAF cells, RK cells, TCMK-1 cells, LLCPK cells, PK15 cells, LLC-RK cells, MDOK cells, BHK cells, BHK-21 cells, CHO cells, CHO-K1 cells, NS-1 cells, MRC-5 cells, WI-38 cells, 3T3 cells, 293 cells, Per.C6 cells and chicken embryo cells. In one embodiment, the cell line is a CHO cell line or one or more of several specific CHO cell variants optimized for large-scale protein production, e.g., CHO-K1.

In one embodiment, the taurine-supplemented cell culture contains insulin, which can be added as a point-of-use ingredient to the media, or can be included in the media formulation. In one embodiment, the cell line comprises cells capable of producing a biotherapeutic protein.

In one embodiment, the media is supplemented at intervals during cell culture according to a fed-batch process. Fed-batch culturing is generally known in the art and employed to optimize protein production (see Y. M. Huang et a/., Biotechnol Prog. 2010 September-October; 26(5): 1400-10), The cell growth phase or seed culture (i.e. a first cell culture) where no exchange of medium is provided, is typically followed by a distinct second culture, known as the polypeptide production phase. Fed-batch processes are typically used during the production phase.

The invention provides a cell culture medium comprising about 0.1 mM to about 10 mM taurine at the start of production cell culture (day 0). Alternatively, cell culture medium comprising about 0.1 mM to about 10 mM taurine may be supplemented on day 1, day 2, day 3, day 4, day 5, day 6, day 7, day 8, day 9, and/or day 10 of the production cell culture. The cell culture medium added to the production culture on multiple days comprises a total amount of taurine between about 0.1 mM to about 10 mM. The cell culture medium comprising total taurine between about 0.1 mM to about 10 mM may be added in any sequential manner.

Taurine may also be supplemented in the basal medium in the seed train expansion phase.

Supplemental feed may be performed to include additional nutrients, such as vitamins, amino acids and other nutrients as described hereinabove, at intervals at a frequency of every day, or every 2-3 days, for the duration of the production culture. Supplemented feed may be performed (supplemented media containing nutrients are added) at least 2 times, or at least 8 times, throughout the duration of the production culture for a 2 week or more culture. In another embodiment, the supplemental feed could be performed on each day for the duration of the culture. Alternative culture feeding schedules are also envisioned.

Additional amino acid supplementation may also be performed to provide a non-depleted medium, wherein depleted amino acids are determined according to methods known in the art and described herein. When this regime is employed, additional amino acids are supplemented or added at intervals, preferably at a frequency of every day, or every 2-3 days, for the duration of the production culture, depending on the determination of amino acid depletion. In one embodiment, the mixture of additional amino acids to maintain a non-depleted cell culture medium is added to the culture on or about day 1, on or about day 2, on or about day 3, on or about day 4, on or about day 5, on or about day 6, on or about day 7, on or about day 8, on or about day 9, on or about day 10, on or about day 11, on or about day 12, on or about day 13, and on or about day 14, for a 2 week or more culture. Alternative culture feeding schedules are also envisioned.

Animal cells, such as CHO cells, may be cultured in small scale cultures, such as in 125 ml containers having about 25 mL of media, 250 mL containers having about 50 to 100 mL of media, 500 mL containers having about 100 to 200 mL of media. Alternatively, the cultures can be large scale such as for example 1000 mL containers having about 300 to 1000 mL of media, 3000 mL containers having about 500 mL to 3000 mL of media, 8000 mL containers having about 2000 mL to 8000 mL of media, and 15000 mL containers having about 4000 mL to 15000 mL of media. Cultures for manufacturing can contain 10,000 L of media or more. Large scale cell cultures, such as for clinical manufacturing of protein therapeutics, are typically maintained for days, or even weeks, while the cells produce the desired protein(s). During this time the culture can be supplemented with a concentrated feed medium containing components, such as nutrients and amino acids, which are consumed during the course of the culture. Concentrated feed medium may be based on any cell culture media formulation. Such a concentrated feed medium can contain most of the components of the cell culture medium at, for example, about 5×, 6×, 7×, 8×, 9×, 10×, 12×, 14×, 16×, 20×, 30×, 50×, 100×, 200×, 400×, 600×, 800×, or even about 1000× of their normal useful amount. Concentrated feed media are often used in fed batch culture processes.

In some embodiments, the cell culture containing taurine is further supplemented with "point-of-use additions", also known as additions, point-of-use ingredients, or point-of-use chemicals, during the course of cell growth or protein production. Point-of-use additions include any one or more of a growth factor or other proteins, a buffer, an energy source, a salt, an amino acid, a metal, and a chelator. Other proteins include transferrin and albumin. Growth factors, which include cytokines and chemokines, are generally known in the art and are known to stimulate cell growth, or in some cases, cellular differentiation. A growth factor is usually a protein (e.g., insulin), a small peptide, or a steroid hormone, such as estrogen, DHEA, testosterone, and the like. In some cases, a growth factor may be a non-natural chemical that promotes cell proliferation or protein production, such as e.g., tetrahydrofolate (THF), methotrexate, and the like. Non-limiting examples of protein and peptide growth factors include angiopoietins, bone morphogenetic proteins (BMPs), brain-derived neurotrophic factor (BDNF), epidermal growth factor (EGF), erythropoietin (EPO), fibroblast growth factor (FGF), glial cell line-derived neurotrophic factor (GDNF), granulocyte colony-stimulating factor (G-CSF), granulocyte macrophage colony-stimulating factor (GM-CSF), growth differentiation factor-9 (GDF9), hepatocyte growth factor (HGF), hepatoma-derived growth factor (HDGF), insulin, insulin-like growth factor (IGF), migration-stimulating factor, myostatin (GDF-8), nerve growth factor (NGF) and other neurotrophins, platelet-derived growth factor (PDGF), thrombopoietin (TPO), transforming growth factor alpha (TGF-a), transforming growth factor beta (TGF-13), tumor necrosis factor-alpha (TNF-a), vascular endothelial growth factor (VEGF), wnt signaling pathway agonists, placental growth factor (PlGF), fetal Bovine somatotrophin (FBS), interleukin-1 (IL-1), IL-2, IL-3, IL-4, IL-5, IL-6, IL-7, and the like. In one embodiment, the cell culture media is supplemented with the point-of-use addition growth factor insulin. In one embodiment, the concentration of insulin in the media, i.e., the amount of insulin in the cell culture media after addition, is from about 0.1 pM to 10 pM.

Buffers are generally known in the art. The invention is not restricted to any particular buffer or buffers, and any one of ordinary skill in the art can select an appropriate buffer or buffer system for use with a particular cell line producing a particular protein. In one embodiment, a point-of-use addition buffer is NaHCO$_3$. In another embodiment, the buffer is HEPES. In other embodiments, the point-of-use addition buffer comprises both NaHCO$_3$ and HEPES.

Energy sources for use as a point-of-use addition in cell culture are also well known in the art. Without limitation, in one embodiment, the point-of-use addition energy source is glucose. Given the particular and specific requirements of a particular cell line and the protein to be produced, in one embodiment the glucose can be added to a concentration of about 1 to 20 mM in the media. In some cases, glucose can be added at high levels of 20 g/L or higher.

Chelators are likewise well known in the art of cell culture and protein production. Tetrasodium EDTA dehydrate and citrate are two common chelators used in the art, although other chelators may be employed in the practice of this invention. In one embodiment, a point-of-use addition chelator is tetrasodium EDTA dihydrate. In one embodiment, a point-of-use addition chelator is citrate, such as Na$_3$C$_6$H$_5$O$_7$.

In one embodiment, the cell culture medium may additionally be supplemented with one or more point-of-use addition amino acids as an energy source, such as e.g., glutamine. In one embodiment, the cell culture media is supplemented with the point-of-use addition glutamine at a final concentration of about 1 mM to 13 mM.

Other point-of-use additions include one or more of various metal salts, such as salts of iron, nickel, zinc and copper. In one embodiment, the cell culture media is supplemented with any one or more of copper sulfate, zinc sulfate, ferric chloride, and nickel sulfate.

In some embodiments, the protein titer yielded from cell culture in taurine supplemented media is at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22% greater, at least 23% greater, at least 24% greater, at least 25% greater, at least 26% greater, at least 27% greater, at least 28% greater or at least 29% greater than the protein titer (yield) from cells cultured in non-taurine supplemented. In some embodiments, the protein titer yielded from cells in taurine supplemented media is at least 2%, at least 3%, at least 4%, or at least 5% greater than the protein titer (yield) from similar or identical cells cultured in non-taurine supplemented media.

In some embodiments, the ammonia accumulation in cell culture is decreased greater than 4%, greater than 5%, greater than 6%, greater than 7%, greater than 8%, greater than 9%, greater than 10%, greater than 15%, or greater than 20% in taurine supplemented media compared to cell culture in non-taurine supplemented media.

Protein Production

In addition to taurine supplemented media and methods of culturing cells in taurine supplemented media, the present invention provides improved methods of producing a protein, such as a therapeutically effective antibody or other biopharmaceutical drug substance, in a cell cultured in taurine supplemented media, The present invention provides a method for producing therapeutic protein in high yield comprising culturing a recombinant cell line in medium containing taurine, wherein the cell line comprises a stably integrated nucleic acid encoding the therapeutic protein.

In some embodiments, the titer (yield) of protein by mammalian cells cultured in medium containing taurine (taurine supplemented medium) is at least 100 mg/L, at least 0.5 g/L, at least 1 g/L, at least 1.2 g/L, at least 1.4 g/L, at least 1.6 g/L, at least 1.8 g/L, at least 2 g/L, at least 2.5 g/L greater than the titer of protein by an identical mammalian cell cultured in non-taurine supplemented medium.

In some embodiments, the protein production yield or titer, which can be expressed in grams of protein product per liter of culture medium, from cells cultured in taurine supplemented medium is at least 100 mg/L, at least 1 g/L, at least 1.2 g/L, at least 1.4 g/L, at least 1.6 g/L, at least 1.8 g/L, at least 2 g/L, at least 2.5 g/L, at least 3 g/L, at least, 3.5 g/L, at least 4 g/L, at least 4.5 g/L, at least 5 g/L, at least 5.5 g/L, at least 6 g/L, at least 6.5 g/L, at least 7 g/L, at least 7.5 g/L, at least 8 g/L, at least 8.5 g/L, at least 9 g/L, at least 9.5 g/L, at least 10 g/L, at least 15 g/L, or at least 20 g/L.

In some embodiments, the protein titer yielded from cells in taurine supplemented media is at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23% greater, at least 24% greater, at least 25% greater, at least 26% greater, at least 27% greater, at least 28% greater or at least 29% greater than the protein titer (yield) from similar or identical cells cultured in non-taurine supplemented media.

In some embodiments, the protein product (protein of interest) is an antibody, a human antibody, a humanized antibody, a chimeric antibody, a monoclonal antibody, a multispecific antibody, a bispecific antibody, an antigen binding antibody fragment, a single chain antibody, a diabody, triabody or tetrabody, a Fab fragment or a F(ab')2 fragment, an IgD antibody, an IgE antibody, an IgM antibody, an IgG antibody, an IgG1 antibody, an IgG2 antibody, an IgG3 antibody, or an IgG4 antibody. In one embodiment, the antibody is an IgG1 antibody. In one embodiment, the antibody is an IgG2 antibody. In one embodiment, the antibody is an IgG4 antibody. In one embodiment, the antibody is a chimeric IgG2/IgG4 antibody. In one embodiment, the antibody is a chimeric IgG2/IgG1 antibody. In one embodiment, the antibody is a chimeric IgG2/IgG1/IgG4 antibody.

In some embodiments, the antibody is selected from the group consisting of an anti-Programmed Cell Death 1 antibody (e.g. an anti-PD1 antibody as described in U.S. Pat. Appln. Pub. No. US2015/0203579A1), an anti-Programmed Cell Death Ligand-1 (e.g. an anti-PD-L1 antibody as described in in U.S. Pat. Appln. Pub. No. US2015/0203580A1), an anti-Dll4 antibody, an anti-Angiopoetin-2 antibody (e.g. an anti-ANG2 antibody as described in U.S. Pat. No. 9,402,898), an anti-Angiopoetin-Like 3 antibody (e.g. an anti-AngPtl3 antibody as described in U.S. Pat. No. 9,018,356), an anti-platelet derived growth factor receptor antibody (e.g. an anti-PDGFR antibody as described in U.S. Pat. No. 9,265,827), an anti-Erb3 antibody, an anti-Prolactin Receptor antibody (e.g. anti-PRLR antibody as described in U.S. Pat. No. 9,302,015), an anti-Complement 5 antibody (e.g. an anti-05 antibody as described in U.S. Pat. Appln. Pub. No US2015/0313194A1), an anti-TNF antibody, an anti-epidermal growth factor receptor antibody (e.g. an anti-EGFR antibody as described in U.S. Pat. No. 9,132,192 or an anti-EGFRvIII antibody as described in U.S. Pat. Appln. Pub. No. US2015/0259423A1), an anti-Proprotein Convertase Subtilisin Kexin-9 antibody (e.g. an anti-PCSK9 antibody as described in U.S. Pat. No. 8,062,640 or U.S. Pat. Appln. Pub. No. US2014/0044730A1), an anti-Growth And Differentiation Factor-8 antibody (e.g. an anti-GDF8 antibody, also known as anti-myostatin antibody, as described in U.S. Pat. No. 8,871,209 or U.S. Pat. No. 9,260,515), an anti-Glucagon Receptor (e.g. anti-GCGR antibody as described in U.S. Pat. Appln. Pub. Nos. US2015/0337045A1 or US2016/0075778A1), an anti-VEGF antibody, an anti-IL1R antibody, an interleukin 4 receptor antibody (e.g an anti-IL4R antibody as described in U.S. Pat. Appln. Pub. No. US2014/0271681A1 or U.S. Pat. No. 8,735,095 or U.S. Pat. No. 8,945,559), an anti-interleukin 6 receptor antibody (e.g. an anti-IL6R antibody as described in U.S. Pat. Nos. 7,582,298, 8,043,617 or 9,173,880), an anti-IL1 antibody, an anti-IL2 antibody, an anti-IL3 antibody, an anti-IL4 antibody, an anti-IL5 antibody, an anti-IL6 antibody, an anti-IL7 antibody, an anti-interleukin 33 (e.g. anti-IL33 antibody as described in U.S. Pat. Appln. Pub. Nos. US2014/0271658A1 or US2014/0271642A1), an anti-Respiratory syncytial virus antibody (e.g. anti-RSV antibody as described in U.S. Pat. Appln. Pub. No. US2014/0271653A1), an anti-Cluster of differentiation 3 (e.g. an anti-CD3 antibody, as described in U.S. Pat. Appln. Pub. Nos. US2014/0088295A1 and US20150266966A1, and in U.S. Application No. 62/222,605), an anti-Cluster of differentiation 20 (e.g. an anti-CD20 antibody as described in U.S. Pat. Appln. Pub. Nos. US2014/0088295A1 and US20150266966A1, and in U.S. Pat. No. 7,879,984), an anti-CD19 antibody, an anti-CD28 antibody, an anti-Cluster of Differentiation-48 (e.g. anti-CD48 antibody as described in U.S. Pat. No. 9,228,014), an anti-Fel dl antibody (e.g. as described in U.S. Pat. No. 9,079,948), an anti-Middle East Respiratory Syndrome virus (e.g. an anti- MERS antibody as described in U.S. Pat. Appln. Pub. No. US2015/0337029A1), an anti-Ebola virus antibody (e.g. as described in U.S. Pat. Appln Pub. No. US2016/0215040), an anti-Zika virus antibody, an anti-Lymphocyte Activation Gene 3 antibody (e.g. an anti-LAG3 antibody, or an anti-CD223 antibody), an anti-Nerve Growth Factor antibody (e.g. an anti-NGF antibody as described in U.S. Pat. Appln. Pub. No. US2016/0017029 and U.S. Pat. Nos. 8,309,088 and 9,353,176) and an anti-Activin A antibody. In some embodiments, the bispecific antibody is selected from the group consisting of an anti-CD3× anti-CD20 bispecific antibody (as described in U.S. Pat. Appln. Pub. Nos. US2014/0088295A1 and US20150266966A1), an anti-CD3× anti-Mucin 16 bispecific antibody (e.g., an anti-CD3× anti-Muc16 bispecific antibody), and an anti-CD3× anti-Prostate-specific membrane antigen bispecific antibody (e.g., an anti-CD3× anti-PSMA bispecific antibody). In some embodiments, the protein of interest is selected from the group consisting of alirocumab, sarilumab, fasinumab, nesvacumab, dupilumab, trevogrumab, evinacumab, and rinucumab. All publications mentioned throughout this disclosure are incorporated herein by reference in their entirety.

In some embodiments, the protein of interest is a recombinant protein that contains an Fc moiety and another domain, (e.g., an Fc-fusion protein). In some embodiments, an Fc-fusion protein is a receptor Fc-fusion protein, which contains one or more extracellular domain(s) of a receptor coupled to an Fc moiety. In some embodiments, the Fc moiety comprises a hinge region followed by a CH2 and CH3 domain of an IgG. In some embodiments, the receptor Fc-fusion protein contains two or more distinct receptor chains that bind to either a single ligand or multiple ligands. For example, an Fc-fusion protein is a TRAP protein, such as for example an IL-1 trap (e.g., rilonacept, which contains the IL-1RAcP ligand binding region fused to the Il-1R1 extracellular region fused to Fc of hIgG1; see U.S. Pat. No. 6,927,004, which is herein incorporated by reference in its entirety), or a VEGF trap (e.g., aflibercept or ziv-aflibercept, which contains the Ig domain 2 of the VEGF receptor Flt1 fused to the Ig domain 3 of the VEGF receptor Flk1 fused to Fc of hIgG1: see U.S. Pat. Nos. 7,087,411 and 7,279,159). In other embodiments, an Fc-fusion protein is a ScFv-Fc-fusion protein, which contains one or more of one or more antigen-binding domain(s), such as a variable heavy chain fragment and a variable light chain fragment, of an antibody coupled to an Fc moiety.

The present invention is not limited to any particular type of cell for protein production. Examples of cell types suitable for protein production include mammalian cells, insect cells, avian cells, bacterial cells, and yeast cells. The cells may be stem cells or recombinant cells transformed with a vector for recombinant gene expression, or cells transfected with a virus for producing viral products. The cells may contain a recombinant heterologous polynucleotide construct that encodes a protein of interest. That construct can be an episome or it can be an element that is physically integrated into the genome of the cell. The cells may also produce a protein of interest without having that protein encoded on a heterologous polypeptide construct. In other words, the cell may naturally encode the protein of interest, such as a B-cell producing an antibody. The cells may also be primary cells, such as chicken embryo cells, or primary cell lines. Examples of useful cells include BSC cells, LLC-MK cells, CV-1 cells, COS cells, VERO cells, MDBK cells, MDCK cells, CRFK cells, RAF cells, RK cells, TCMK-1 cells, LLCPK cells, PK15 cells, LLC-RK cells, MDOK cells, BHK-21 cells, chicken embryo cells, NS-1 cells, MRC-5 cells, WI-38 cells, BHK cells, 293 cells, RK cells, Per.C6 cells and CHO cells. In various embodiments, the cell line is a CHO cell derivative, such as CHO-K1, CHO DUX B-11, CHO DG-44, Veggie-CHO, GS-CHO, S-CHO, or CHO lec mutant lines.

In one embodiment, the cell, which is a CHO cell, ectopically expresses a protein. In one embodiment, the protein comprises an immunoglobulin heavy chain region, such as a CH1, CH2, or CH3 region. In one embodiment, the protein comprises a human or rodent immunoglobulin CH2 and CH3 region. In one embodiment, the protein comprises a human or rodent immunoglobulin CH1, CH2, and CH3 region. In one embodiment, the protein comprises a hinge region and a CH1, CH2, and CH3 region. In one embodiment, the protein comprises an immunoglobulin heavy chain variable domain. In one embodiment, the protein comprises an immunoglobulin light chain variable domain. In one embodiment, the protein comprises an immunoglobulin heavy chain variable domain and an immunoglobulin light chain variable domain. In one embodiment, the protein is an antibody, such as a human antibody, a rodent antibody, or a chimeric human/rodent antibody (e.g., human/mouse, human/rat, or human hamster).

A production phase can be conducted at any scale of culture, from shaker flasks or wave bags, to one-liter bioreactors, and to large scale industrial bioreactors. Likewise, a seed train expansion phase can be conducted at any scale of culture, from and shaker flasks or wave bags, to one-liter or larger bioreactors. A large scale process can be conducted in a volume of about 100 liters to 20,000 liters or more. One or more of several means may be used to control protein production, such as temperature shift or chemical induction. A growth phase may occur at a higher temperature than a production phase. For example, a growth phase may occur at a first temperature of about 35° C. to 38° C., and a production phase may occur at a second temperature of about 29° C. to 37° C., optionally from about 30° C. to 36° C. or from about 30° C. to 34° C. In addition, chemical inducers of protein production, such as caffeine, butyrate, tamoxifen, estrogen, tetracycline, doxycycline, and hexamethylene bisacetamide (HMBA), may be added concurrent with, before, or after a temperature shift. If inducers are added after a temperature shift, they can be added from one hour to five days after the temperature shift, such as from one to two days after the temperature shift. Production cell cultures may be run as continuous feed culture system, as in a chemostat (see C. Altamirano et al., 2001 supra), or according to a fed-batch process (Huang, 2010 supra).

The invention is useful for improving protein production via cell culture processes. The cell lines used in the invention can be genetically engineered to express a polypeptide of commercial or scientific interest. Genetically engineering the cell line involves transfecting, transforming or transducing the cells with a recombinant polynucleotide molecule, or otherwise altering (e.g., by homologous recombination and gene activation or fusion of a recombinant cell with a non-recombinant cell) so as to cause the host cell to express a desired recombinant polypeptide. Methods and vectors for genetically engineering cells or cell lines to express a polypeptide of interest are well known to those of skill in the art; for example, various techniques are illustrated in Current Protocols in Molecular Biology. Ausubel et al., eds. (Wiley & Sons, New York, 1988, and quarterly updates); Sambrook et al., Molecular Cloning: A Laboratory Manual (Cold Spring Laboratory Press, 1989); Kaufman, R. J., Large Scale Mammalian Cell Culture, 1990, pp. 15-69. A wide variety of cell lines suitable for growth in culture are available from the American Type Culture Collection (Manassas, Va.) and commercial vendors. Examples of cell lines commonly used in the industry include VERO, BHK, HeLa, CVI (including Cos), MDCK, 293, 3T3, myeloma cell lines (e.g., NSO, NSI), PC12, WI38 cells, and Chinese hamster ovary (CHO) cells. CHO cells are widely used for the production of complex recombinant proteins, such as cytokines, clotting factors, and antibodies (Brasel et al. (1996), Blood 88:2004-2012; Kaufman et al. (1988), J. Biol Chem 263:6352-6362; McKinnon et al. (1991), J Mol Endocrinol 6:231-239; Wood et al. (1990), J Immunol. 145:3011-3016). The dihydrofolate reductase (DHFR)-deficient mutant cell lines (Urlaub et al. (1980), Proc Natl Acad Sci USA 77: 4216-4220), DXBI 1 and DG-44, are desirable CHO host cell lines because the efficient DHFR selectable and amplifiable gene expression system allows high level recombinant protein expression in these cells (Kaufman RJ. (1990), Meth Enzymol 185:537-566). In addition, these cells are easy to manipulate as adherent or suspension cultures and exhibit relatively good genetic stability. CHO cells and the proteins recombinantly expressed by them have been extensively characterized and have been approved for use in clinical and commercial manufacturing by regulatory agencies. In some embodiments, the CHO cell lines are cell lines as described in U.S. Patent Application Publication Nos. 2010/0304436 A1, 2009/0162901 A1 and 2009/0137416 A1, and U.S. Pat. Nos. 7,455,988 B2, 7,435,553 B2, and 7,105,348 B2.

The present invention is not limited in scope by the specific embodiments described herein, which are intended as illustrations of individual aspects or embodiments of the invention. Functionally equivalent methods and components are within the scope of the invention. Various modifications of the invention, in addition to those described here, are apparent to those skilled in the art from the foregoing description and accompanying drawings. Such modifications fall within the scope of the invention.

EXAMPLES

Example 1: Improved Antibody Titers Due to Taurine Supplementation

Example 1A—High-Throughput Shake Flask Culture: 250 mL shake flasks were inoculated from a seed culture of a monoclonal antibody (Ab1) producing cell line derived from CHO-K1. The inoculated cells were grown at 35.5° C. for seventeen days and fed glucose and other supplemental nutrients as needed. Cells were grown in chemically defined (hydrolysate-free and serum-free) base media.

Each culture flask was either unsupplemented (Flask 1a), or supplemented with 1 mM taurine at day 0 (Flask 1 b).

TABLE 2

Average 17-Day Antibody Titers (g/L) and Approximate Titer Increase (%) Relative to Baseline

| Flask | Medium Supplement | Ab1 Titer | |
|-------|-------------------|-----------|---|
| 1a | Unsupplemented* | 7.3 g/L | |
| 1b | Taurine | 7.9 g/L^ | 8% |

*Baseline control for % titer increase: Flask 1Hb compared to titer in unsupplemented media (Flask 1a).
^Difference in final titer between unsupplemented and supplemented culture is statistically significant (p < 0.05).

Titer values were calculated from protein harvested on day 17, and are statistically significant (p<0.05) compared to baseline. Taurine-supplemented cultures exhibit an overall 8% increase in final protein titer over unsupplemented cultures.

Example 1B—Benchtop-Scale Bioreactors: In a similar example, yet on a larger scale of production, 2 L bioreactors were inoculated from a seed culture of a monoclonal antibody (Ab2, Ab3 or Ab4) producing cell line derived from CHO-K1. The inoculated cultures were grown at a temperature of 35.5° C., DO set point of 40.4% and air sparge of 22 ccm for 14 days. Ab2 and Ab3 processes had pH setpoints of 7.0 f 0.15, while the Ab4 process had a pH setpoint of 7.13±0.27. Glucose, antifoam and basal feed were supplied to the bioreactors as needed. Cultures were grown in unsupplemented medium (Bioreactor 2a, 3a. 4a) or grown in about 1 mM taurine-supplemented medium (Ab2 and Ab3) or about 3 mM taurine-supplemented medium (Ab4), added on day 0 of production (Bioreactors 2b, 3b and 4b, respectively).

Antibody yield (titer) was 6.4 g/L for Ab2-producing cells, yet the cells grown with taurine yielded 8 g/L protein. The 24% increase in titer compared to cells grown without taurine supplementation is statistically significant (p<0.05). The resulting final titers for Ab3-producing cultures and Ab4-producing cultures are also significantly higher (p<0.05) after 14 days (11% and 20%, respectively). compared to non-taurine supplemented cultures. See Table 3.

TABLE 3

Average 14 Day Antibody Titers (g/L) and Approximate Titer Increase (%) Relative to Baseline

| Medium Supplement | Bioreactor # | Ab2 Titer | | Bioreactor # | Ab3 Titer | | Bioreactor # | Ab4 Titer | |
|---|---|---|---|---|---|---|---|---|---|
| Unsupplemented* | 2a | 6.4 g/L | | 3a | 6.6 g/L | | 4a | 4.4 g/L | |
| Taurine | 2b | 8 g/L^ | 24% | 3b | 7.3 g/L^ | 11% | 4b | 5.3 g/L^ | 20% |

*Unsupplemented medium is the baseline control for % titer increase, where Bioreactors 2b, 3b, or 4b % titer increase is compared to titer in unsupplemented media (Bioreactors 2a, 3a, or 4a, respectively).
^Differences in final titer between supplemented and unsupplemented cultures are statistically significant (p < 0.05).

A timecourse with regard to protein titer was plotted for the Ab3-producing cell culture and significant improvement in protein titer due to taurine supplementation was observed at each day of culture, starting at day 6.

TABLE 4

Antibody Titer (g/L) Improvement Due to Taurine Supplementation at Representative Timepoints

| Bio-reactor | Media Supplement | Ab3 Titer at day 6 | | Ab3 Titer at day 9 | | Ab3 Titer at day 14 | |
|---|---|---|---|---|---|---|---|
| 3a | Unsupplemented* | 1.7 g/L | | 4.1 g/L | | 6.6 g/L | |
| 3b | Taurine | 1.9 g/L | 12% | 5.3 g/L^ | 29% | 7.3 g/L^ | 11% |

*Approximate increase (%) compared to unsupplemented medium collected on same day
^Increase in titer with taurine supplementation is statistically significant ($p < 0.05$) compared to unsupplemented culture.

A significant improvement in titer could be seen in production culture as early as day 6 (12% increase compared to the same culture without taurine supplementation). See also FIG. 1. The maximum difference in this timecourse was seen at day 9 (significant ($p < 0.05$) increase of 29% in Bioreactor 3b compared to 3a), and significant ($p < 0.05$) titer increase of 11% was observed on the final day (14) of culture.

The protein production benefits of taurine-supplementation are observed across different scales (Example 1A and 1B) and different cell lines (Example 1B).

Example 2: Consistent Productivity with Varying Taurine Concentrations in a High-Throughput Shake Flask Culture Consistency of the protein titer was tested by varying the amount of taurine added to the culture at production day 0. 250 mL shake flasks were inoculated from a seed culture of a monoclonal antibody (Ab1) producing cell line derived from CHO-K1. The inoculated cells were grown at 35.5° C. for fourteen days and fed glucose and other supplemental nutrients as needed. Cells were grown in chemically defined (hydrolysate-free and serum-free) base media.

Each culture contained either no taurine (unsupplemented) or taurine at 0.1 mM, 0.3 mM, 0.5 mM, 0.7 mM, 1 mM, 3 mM, 5 mM, 7.5 mM or 10 mM concentrations.

TABLE 5

Average 14-Day Antibody Titers (g/L) for Cultures Supplemented with 0.1 to 10 mM Taurine

| Shake Flask | Media Supplement | Ab1 Titer | |
|---|---|---|---|
| 5a | Unsupplemented* | 6.5 g/L | |
| 5b | 0.1 mM Taurine# | 6.7 g/L | 3% |
| 5c | 0.3 mM Taurine^ | 6.8 g/L | 5% |
| 5d | 0.5 mM Taurine^ | 6.9 g/L | 6% |
| 5e | 0.7 mM Taurine^ | 7.0 g/L | 8% |
| 5f | 1 mM Taurine^ | 7.0 g/L | 8% |
| 5g | 5 mM Taurine^ | 7.1 g/L | 9% |
| 5h | 7.5 mM Taurine^ | 7.1 g/L | 9% |
| 5i | 10 mM Taurine^ | 7.1 g/L | 9% |

*Unsupplemented medium is the baseline control for % titer increase
Difference in final titer is statistically significance compared to unsupplemented control ($p < 0.1$).
^Difference in final titer is statistically significance compared to unsupplemented control ($p < 0.05$).

It is shown that varying the amount of taurine-supplementation consistently produces high titers, when taurine is supplemented in a range of at least 0.1 mM to 10 mM. Final titers for the taurine supplemented conditions were statistically different from the unsupplemented condition. For 0.1 mM taurine, $p < 0.1$ while $p < 0.05$ for 0.3 mM to 10 mM taurine.

Example 3: Testing Varying Taurine Feeding Schedules in a High-Throughput Shake Flask Culture

Example 3A: Addition of Taurine During Seed Train Expansion Phase

The benefits of adding taurine to the culture during the expansion seed train phase were assessed in the high-throughput shake flask model. In flask 6a (Table 6), the Ab1-producing CHO cells were thawed in chemically defined (hydrolysate-free and serum-free) base media supplemented with 1 mM taurine. Taurine concentration of basal medium was maintained at 1 mM throughout the expansion phase. During production, the culture basal medium was supplemented with 1 mM taurine on day 0. Glucose and nutrient basal feed were supplied as needed during the 17 day production.

Flask 6b cells grew in taurine-free (unsupplemented) chemically defined (hydrolysate-free and serum-free) basal medium throughout the seed train expansion phase. At day 0 of production, the culture basal medium was supplemented with 1 mM taurine. For the 17 day production, glucose and nutrient basal feeds were supplied as needed.

TABLE 6

Average 17-Day Antibody Titers for Cultures Supplemented with 1 mM Taurine during Different Phases of the Process

| Shake Flask | Addition of 1 mM Taurine | Ab1 Titer |
|---|---|---|
| 6a | Seed Train and Production Phases | 7.7 g/L |
| 6b | Only Production Phase | 7.8 g/L |

Differences in final titer (day 17) are not statistically significant ($p > 0.1$).

Final (day 17) titer values for both conditions (taurine supplementation in production only or seed train and production combined) are similar. Resulting titers are not statistically significant ($p > 0.1$). The benefit of adding taurine in the seed train expansion phase is analogous to supplementing taurine in the production phase.

Example 3B: Varying Taurine Feeding Schedules during Production Phase: To determine whether varying standard feeding schedules of taurine had any effect on the protein titer for taurine-supplemented cultures, additional experiments were conducted in analogous shake flask cultures growing Ab1-producing CHO cells. The cells were subjected to varying culture conditions similar to Example 2, where the feeding schedule was the same as before, glucose/nutrient basal feed was added as needed.

Ab1-producing cultures were supplemented with a total of 5 mM taurine Similar productivity (7.1 g/L, 6.8 g/L and 7.0 g/L) is observed in varying taurine feeding schedules. Titer values as compared in this experiment are not statistically different (p>0.1) (see Table 7).

TABLE 7

Average 14-Day Antibody Titers (g/L) for Cultures Supplemented with 5 mM Taurine with Varying Schedules

| Taurine Schedule | Ab1 Day 14 Titer |
|---|---|
| 5 mM day 0 | 7.1 g/L |
| 1 mM days 0, 3, 5, 7, 10 (5 mM total) | 6.8 g/L |
| 1 mM day 0; 2 mM days 7, 10 (5 mM total) | 7.0 g/L |

Differences between day 14 titer values are not statistically significant (p > 0.1).

The feeding schedules of taurine do not have any negative effect, nor alter the outcome where taurine-supplementation is beneficial to product yield. Thus, taurine supplementation may be added once at day 0, or added on subsequent days of the production phase, or may be added at multiple intervals during the production phase.

Example 4: Measuring Ammonia Byproduct in a High-Throughput Shake Flask Culture

Ammonia by-product was measured following 14-day cultures conducted in an analogous manner as Example 2 for taurine-supplemented cultures of Ab1-producing CHO cells. The cells were subjected to varying culture conditions similar to above where glucose/nutrient base feed was added as needed.

TABLE 8

Average 17-Day Ammonia (mM) and Decrease (%)

| Media Supplement | Ab1 Ammonia | |
|---|---|---|
| Unsupplemented* | 2.56 mM | |
| Taurine | 1.73 mM" | −32% |

*Baseline control for % ammonia decrease: taurine supplemented condition compared to ammonia in unsupplemented medium.
"Decrease in ammonia concentration is statistically significant (p < 0.1).

In the Ab1-producing cells, taurine supplementation in the medium supports a healthy, sustainable culture where the ammonia by-product has been reduced by 32%. The decrease in ammonia concentration from taurine supplementation is statistically significant (p<0.1).

The present invention may be embodied in other specific embodiments.

What is claimed is:

1. A method for culturing recombinant eukaryotic cells for improved production of dupilumab, comprising the steps of:
   (a) propagating recombinant eukaryotic cells in a defined cell culture medium during a growth phase, wherein said cell culture medium is free of glutamine;
   (b) supplementing the defined cell culture medium with about 0.1 mM to about 10 mM L-taurine and one or more of the following: 0 mM to 11.2 mM alanine, 2.4 mM to 11.9 mM arginine, 1.3 mM to 33.3 mM asparagine, 1.5 mM to 93.9 mM aspartic acid, 1.1 mM to 19.9 mM cysteine, 1.4 mM to 47.6 mM glutamic acid, 0 mM to 16.7 mM glycine, 1 mM to 9.5 mM histidine, 1.5 mM to 22.9 mM isoleucine, 1.5 mM to 38.1 mM leucine, 2.7 mM to 24.6 mM lysine, 1.3 mM to 13.4 mM methionine, 1.2 mM to 18.2 mM phenylalanine, 1.7 mM to 26.1 mM proline, 1.9 mM to 57.1 mM serine, 1.7 mM to 33.6 mM threonine, 0.5 mM to 14.7 mM tryptophan, 0.9 mM to 22.2 mM tyrosine, and 1.7 mM to 34.1 mM valine; and
   (c) expressing dupilumab during a production phase, wherein the addition of L-taurine increases the titer of dupilumab by at least 3% when compared to cells expressing dupilumab in a cell culture medium containing less than 0.1 mM L-taurine.

2. The method of claim 1, wherein said cell culture medium is serum-free.

3. The method of claim 1, wherein a total amount of amino acids or amino acid salts with which the defined cell culture medium is supplemented does not exceed 115 mM.

4. The method of claim 1, further comprising the step of supplementing said cell culture medium with ≤16 g/L hydrolysate.

5. The method of claim 1, further comprising the step of supplementing said cell culture medium with fatty acids.

6. The method of claim 1, further comprising the step of supplementing said cell culture medium with nucleosides including one or more of the following: adenosine, guanosine, cytidine, uridine, thymidine, and hypoxanthine.

7. The method of claim 1, further comprising the step of supplementing said cell culture medium with salts of calcium, magnesium, and phosphate.

8. The method of claim 1, wherein the taurine supplement is further provided at least three additional times during the production phase.

9. The method of claim 1, wherein the taurine supplement is provided on each day for the duration of the production phase.

10. The method of claim 1, wherein the defined cell culture medium is supplemented with about 0.09 mM to about 0.9 mM ornithine.

11. The method of claim 1, wherein the eukaryotic cells are CHO cells.

12. The method of claim 1, wherein said cells are maintained at a first temperature of 35° C. to 38° C. during said growth phase and a second temperature of 29° C. to 37° C. during said production phase, wherein the first temperature is higher than the second temperature.

13. A method for culturing recombinant eukaryotic cells for improved production of dupilumab, comprising the steps of:
   (a) propagating cells in a defined cell culture medium during a growth phase; and
   (b) supplementing the defined cell culture medium with about 0.1 mM to about 10 mM L-taurine and expressing dupilumab during a production phase,
   wherein the addition of L-taurine increases the titer of the dupilumab by at least 7% when compared to cells expressing dupilumab in a cell culture medium containing less than 0.1 mM L-taurine, and wherein said propagating cells during said growth phase is performed at a temperature of about 35° C. to 38° C., and said expressing dupilumab during said production phase is performed at a temperature of about 29° C. to 37° C., wherein the temperature of said growth phase is higher than the temperature of said production phase.

14. The method of claim 13, wherein the L-taurine is supplemented from about 1 to about 5 times during the production phase.

15. The method of claim 13, wherein the L-taurine is supplemented on each day for the duration of the production phase.

16. The method of claim 13, further comprising supplementing the defined cell culture medium with about 0.1 mM to about 10 mM L-taurine during the growth phase.

17. The method of claim 13, wherein the defined cell culture medium is supplemented with about 0.09 mM to about 0.9 mM ornithine.

18. The method of claim 13, wherein the eukaryotic cells are CHO cells.

19. A method for producing dupilumab comprising the steps of:
(a) culturing cells expressing dupilumab in a cell culture medium comprising about 0.1 mM to about 10 mM L-taurine, wherein the addition of L-taurine increases the titer of the dupilumab by at least 3% to 7% when compared to cells expressing dupilumab in a cell culture medium containing less than 0.1 mM L-taurine; and
(b) producing dupilumab in the cell, wherein the dupilumab is secreted into the medium,
wherein said cells are cultured at a temperature of about 35° C. to 38° C. during a growth phase and about 29° C. to 37° C. during a production phase, wherein the temperature of the growth phase is higher than the temperature of the production phase.

20. The method of claim 19, wherein the cells are capable of about 7% or greater increase in titer of dupilumab compared to cells expressing dupilumab in a cell culture medium containing less than 0.1 mM L-taurine.

21. The method of claim 19, wherein the cells are CHO cells.

22. The method of claim 19, further comprising supplementing the cell culture medium with about 0.09 mM to about 0.9 mM ornithine.

23. A method for producing dupilumab comprising culturing a recombinant cell line in a cell culture medium comprising at least about 0.1 mM L-taurine, wherein the recombinant cell line comprises a stably integrated nucleic acid encoding dupilumab, and producing dupilumab from the cells, wherein the addition of L-taurine to the cell culture medium increases the titer of the dupilumab by at least 3% to 7% when compared to culturing the recombinant cell line in a cell culture medium containing less than 0.1 mM L-taurine, and wherein said recombinant cell line is cultured at a temperature of about 35° C. to 38° C. during a growth phase and about 29° C. to 37° C. during a production phase, wherein the temperature of the growth phase is higher than the temperature of the production phase.

24. The method of claim 23, wherein the production method is capable of increasing the dupilumab titer by at least 0.1 g/L, at least 0.5 g/L, at least 1 g/L, at least 1.2 g/L, at least 1.4 g/L, at least 1.6 g/L, at least 1.8 g/L, at least 2 g/L, at least 2.2 g/L, at least 2.4 g/L, or at least 2.5 g/L compared to a similar production method in a cell culture medium that contains less than 0.1 mM L-taurine.

25. The method of claim 23, wherein the production method is capable of increasing the dupilumab titer by about 7% or greater compared to a similar production method in a cell culture medium that contains less than 0.1 mM L-taurine.

26. The method of claim 23, wherein the recombinant cell line is cultured in the cell culture medium comprising at least about 0.1 mM L-taurine for at least 6 days and expresses a higher titer of dupilumab compared to a recombinant cell line expressing dupilumab cultured in the cell culture medium for at least 6 days in the absence of L-taurine.

27. The method of claim 23, further comprising supplementing the cell culture medium with about 0.09 mM to about 0.9 mM ornithine.

28. The method of claim 26, wherein the titer of dupilumab from the cells expressing dupilumab cultured in the cell culture medium comprising at least about 0.1 mM L-taurine for at least 6 days is at least 8%, 9%, 10%, 11%, 12%, 13%, 14%, 15%, or at least 20% higher than the titer of dupilumab from the cells cultured in the cell culture medium for at least 6 days in the absence of L-taurine.

29. The method of claim 23, wherein the cells are CHO cells.

* * * * *